(12) United States Patent
Gray et al.

(10) Patent No.: US 6,300,066 B1
(45) Date of Patent: Oct. 9, 2001

(54) Y CHROMOSOME SPECIFIC NUCLEIC ACID PROBE AND METHOD FOR DETERMINING THE Y CHROMOSOME IN SITU

(75) Inventors: Joe W. Gray, San Francisco; Heinz-Ulrich Weier, Oakland, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/197,948

(22) Filed: Nov. 23, 1998

Related U.S. Application Data

(60) Continuation of application No. 08/546,452, filed on Oct. 6, 1995, now Pat. No. 5,888,730, which is a division of application No. 07/594,921, filed on Oct. 10, 1990, now Pat. No. 5,840,482.

(51) Int. Cl.[7] ...................................................... C12Q 1/68
(52) U.S. Cl. ............................................... 435/6; 536/23.1
(58) Field of Search ................................. 435/6; 536/23.1

(56) References Cited

U.S. PATENT DOCUMENTS 4,683,195 * 7/1987 Mullis et al. .............................. 435/6
5,055,393 * 10/1991 Kwoh et al. .............................. 435/6

OTHER PUBLICATIONS

Nakahori et al., Nuc. Acids Res. 14(19):7569–7580, 1986.*
Wallace et al., Methods Enzymol. 12:432–442, 1987.*
Weier et al., Am. J. of Human Genetics, suppl. vol. 43(3):A253, 1007; 19, 163, Sep. 1988.*
Goonewardena et al., Amer. J. Human Genet. 45(4):A190, Oct. 1989.*

* cited by examiner

*Primary Examiner*—Scott W. Houtteman
(74) *Attorney, Agent, or Firm*—William E. Murray

(57) ABSTRACT

A method for producing a Y chromosome specific probe selected from highly repeating sequences on that chromosome is described. There is little or no nonspecific binding to autosomal and X chromosomes, and a very large signal is provided. Inventive primers allowing the use of PCR for both sample amplification and probe production are described, as is their use in producing large DNA chromosome painting sequences.

12 Claims, 9 Drawing Sheets

(2 of 9 Drawing Sheet(s) Filed in Color)

FIG. 1

```
TTCCATTCCA TTCCAATCCA TTCCTTTCCT TTCGCTTGCA TTCCATTCTA TTCCCTTCTA CTGCATACAA    70
TTTCACTCCA TTCGTTCCCA TTCCATTCAA TTCCATTCCA TTCAATTCCA TTCCATTTGT TTCCATTCTC   140
TTCGATTCCA TTTCTTTATA TTCCATGCCA TTCGATTCCA TTCTATTGGA TTGCATTACA TACGTGTTCA   210
TTCCATTCCA GACGATTCCA TTTGACTCCA TTCCTTTCGA GCCCTTTCAA TTTGAGTCCA TTCCTTTCCA   280
GTCCATTTCA CTCCAGTCCA TTACTATCCA TTCCATACCA TTCCATCCCA TTCCATTCCA TTCCATTCCA   350
TTCCATTCCA TTGCATTCCA TTCCATTCCA TTCCATTCCA TTCCATTCCA TTGCACTGCA CTCCATTCCA   420
TTACATTCTA CTCTATCTGA GTCGATTTTA TTGCATTAGA TTCTATTCCA TTGGATTACT TTCCATTCGA   490
TTACATTCCA TTCATGTACA TTCCATTCCA GTCAATTACA TTCGAGTTCA TTACATTACA TTCCAGTATA   560
TTCCATTGTA TTCGATCCCA TTCCTTTCAA TTCCATTTCA TTCGACTCCA TTATATTCGA TTCCATTCCA   630
CTCGAATCCA TTCCATTAGA GGACATTCCA TTCCAATGCA TTCCATTCCA TTCCATAGCA TTCCATTGCA   700
TTCGATTCCA TTCCATTTGA TGCCATTCCA TTTGATGCCA TTCCATGACA TTCCATTCCA TTCGAGTCCG   770
TTCCGTTCCA ATTCATTGCA TTCCGTTTCA TGAAATTCGA GTCCTTTCCA GTACATTTCA TTCCAATCCC   840
ATCCAATCCA ATCTACTCCA TTCAATTCCT TTCCATTCCA TTTGATTTGA TTCCATTGAT TT-GATTCCA   909
TTCAGTTTGA TTCCATTCCG TGAAATTTCG TTCCATTCTA TTCTATTACA TAACTTTCCA TTCAATTCCA   979
TTCCATTTCA TTTCAGTCCA TTCGCTTCCT TTCCTTTCGA TTCAATTCCA TTTGATTCCA CTCCATTCTA  1049
TGCAATTTCA TTCCAATCGA TTCAATTCCA TTCGATGACA TTCCTTTCGT TTCCATTCCA TTCGAGTCCA  1119
TTCAATTTGA --GCATTCGT GTCCATTCTA TTCGAGTCCA TTCCATTACC GTCTATTCTA TTCCCTTCCA  1187
TTCCTGTTGA TTCAATTTCA TTCCCTTCCA TTCGATTCCT TTCCATTCGA TTCCATTCCT TTCCATTCCA  1257
TTCCATTCGT TCCCATTCCA TGTGATTTCA TTCCATTCCA GTCCATTATA TTCGAGTCCA CTCCACTCCA  1327
TTCTATTACA TTCAATTCCT TTTGAGTCCG TTCCATAACA CTCCATTCAT TTCGATTCCA TTTCTTGACA  1397
G----TTTTC TTCCATTTTA TTCCATTCCG TTCGATTCCA TTCCATTCGA TTGCATTCCA TTCGAATCCT  1463
TTCCATTCCA TTTCATTCCA TTCCTTTCTA TTCCATTCCA TTTCATTCGA TTTGATTCCA TTCTGTTCTA  1533
TTCCATTCAA TTCTTTTTCA TTCCATTCGA ATCCTTTCTA TTGCAGTCCA TTCCATTCGA GTCCATTCCA  1603
ATCCCTTCCA TTCCATTCCA TTACAGTCCA TTCCAATAGA TTCCATTCCT TTGCCTTCCA TTCGAATCCA  1673
TTCCATTCTA GTCCATTCCA TTTGAGTCAA TTCCATTCCA TTCCATTCTA TTCCTTTCCA ATCCATTCGA  1743
TTCCATTCGA TTCAATTCCA TTTGATTCTC TTTCATTCTA TTTTATTCCA TGCCATTTTA TTGCGTTGCA  1813
TTCCATTCCG TTTGATTCCA GTCCATTCAA GAAAGTTCCA TTCCAGTCCA TTGCTTTCCA GTCCATTCCA  1883
TTCCACTCTT GTCTATTCCA CTCCATTCCT TTCCATTCCA TTCCATACTA TTCCATTCCA TTCCTTTGCA  1953
TTCCGT---- TTCCAATCTA TTCGAGTCCA TTGCATTCCA GTCCAATCCA TTCCATTACA TTCCTTTTGG  2019
TTCCCTGCCA GTCGATTGCA TTGCATACTA GACCATTCCA AACCAGTCCA TTCCATTCTA TTTCAACACT  2089
TTCCATTCCA CTCTGTTCGA GTCCATTCCA TTCCAGTCCA TTTAATTCAA GGGCATTCCA TTCCATTCCA  2159
GTCCATTTCA TGTTATTCCA TTCCATTCAA TTCCATTCCA GATGATTCCA TTCCATTCTA TACCATTGCT  2229
CTCTGTTCCA TTCCATTCCA TCTGTCTCCA TTCCTTTCGT TTCGATTCCT TTCCATTCCA TTCCATTACA  2299
TTTGATCCTA TTTTATTAAA TTGCATTCTA TTCGAGTGAT TTCCCTTCGA GTCCTTTCCA TTCAATTCCA  2369
TTCCATTCTA TTCCATTCCT TTGGATTCCA TTCCATTCCG TTCCGTTCAC ATCAATTCCT TGTGATTCCA  2439
TTACATTCGA TTTCTTGCCA TTCGATTCCA TTCCTTTTGA CTCCATTTCA TTCGATTCCA TTCCATTCCA  2509
TTAATTTCCA TTCCATTCGA GACCTTTCCA TTGCAGTCTT TTCCCTTCGA GTCCATTCCG TTCGATTCCC  2579
TTCCATTCGA TTCCATTCCA TTGGAGTCCG TACCAGTCGA GTCCATTCTA TTCCAGTCCA TTAGTTTCGA  2649
CTCCATTGCA TTCGAGTGCA TTCCATTCCG TGGTTGTCCA TTCCATTCCG TTTGATGCCA TTCCATACGA  2719
TTCCATTCAA TTCGAGACGA TTCTATTCCT GTCCATTCCT TGTGGTTCGA TTCCATTTCA CTCTAGTCCA  2789
TTCCATTCCA TTCAATTCCA TTCGACTCTA TTCCGTTCCA TTCAATTCCA TTCCATTCGA TTCCATTTTT  2859
TTCGAGAACC TTCCATTACA CTCCCTTCCA TTCCAGTGCA TTCCATTCCA GTCTCTTCAG TTCGATTCCA  2929
TTCCATTCGT TTCGATTCCT TTCCATTCCA GCCCATTCCA TTCCATTCCA TTCCTTTCCT TTCCGTTTCA  2999
TTAGATTCCA TTGCATTCGA TTCCATTCAA TTCAATTCCG TGCTATTCAA TTTGATTCAT TTCCATTTAA  3069
TTCCATTCCA TTAGATTCCA TTCCGTACGA TTCCATTCCT TTTGAATCCA TTCCATTGGA GTCCATTCAC  3139
TTCCAGAACA TTCCATTCCA GTCGAATCCA TTCGAGTACA TACCATTAAA GTTCATTACA TTCTAATACA  3209
TTCCATTCCA TTGCATTCCA TTCCATTCCA TTAGATGCCA TTCGATTCCA TTCCATGCCA AATCATTGCA  3279
TTCCTTTCCA TTCCGTTCCT ATCAATTCTA TTCCATTCGA TTTAGTTCGA TTCTATTCAC TTCCATTCCA  3349
TTCGATTCCA GTCCATTGGA GTCAATTCCT TTCGACACCC AGCCTTTCCA GTCAATGATT TTGGATTCCA  3419
TTTTTTTGCA TTCCATTACA TTCTATGACA TTCGATTCCG TTTCATTGCA TTCCATTCCA TACATTTTTA  3489
TTCCATTCGA GACCGTAGCA TTCCACTTTA TTCCAGGCCT GTCCATTACA CTACATTCCC TTCCATTCCA  3559
ATGAA                                                                        3564
```

FIG. 3

SYNTHETIC OLIGONUCLEOTIDES USED IN THE EXAMPLES

| | |
|---|---|
| WYR2 | ATT CCG TAC GAT TCC ATT CCT TTT GAA |
| WYR4 | GAA TGT ATT AGA ATG TAA TGA ACT TTA |
| WYR5 | GGA ATC TAA TGG AAT GGA ATT AAA TGG |
| WYR6 | TTC CAT TCC ATT CCA TTC CTT TCC TTT |
| WYR7 | TGG GCT GGA ATG GAA AGG AAT CGA AAC |
| WYR8 | TCC ATT CGA TTC CAT TTT TTT CGA GAA |
| WYR9 | ATG GAA TTG AAT GGA ACG GAA TAG AGT |
| WYR10 | CGA TTC CAT TCA ATT CGA GAC CAT TCT |

1) ALL OLIGONUCLEOTIDES ARE LISTED FROM 5' TO 3'.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)
      (A) DESCRIPTION: nucleic acid primer (iii) HYPOTHETICAL: NO (iv) ANTI-SENSE: NO (viii) POSITION IN GENOME:
      (A) CHROMOSOME/SEGMENT: Y chromosome
      (B) MAP POSITION: 3.4 kb Hae III repeat sequence (ix) FEATURE: Primer for sequence of Y chromosome
      (A) NAME/KEY: primer WYR2
      (C) IDENTIFICATION METHOD: by experiment (xi) SEQUENCE DESCRIPTION: SEQ ID NO:1:

ATTCCGTACG ATTCCATTCC TTTTGAA                                     27

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)
      (A) DESCRIPTION: nucleic acid primer (iii) HYPOTHETICAL: NO (iv) ANTI-SENSE: NO (viii) POSITION IN GENOME:
      (A) CHROMOSOME/SEGMENT: Y chromosome
      (B) MAP POSITION: 3.4 kb Hae III repeat sequence (ix) FEATURE: Primer for sequence of Y chromosome
              (A) NAME/KEY: primer WYR4
              (C) IDENTIFICATION METHOD: by experiment (x) PUBLICATION INFORMATION:
              (A) AUTHORS: Goonewardena, P.
                    Pletcher, B.A.
                    Pergolizzi, R.
                    Bowen, W.T.
              (B) TITLE: Use of PCR with Y-Specific Probes for Rapid
                   Sex Determination
              (C) JOURNAL: American Journal of Human Genetics
              (D) VOLUME: 45
              (E) ISSUE: 4
              (F) PAGES: A190
              (G) DATE: 18-OCT-1990

(xi) SEQUENCE DESCRIPTION: SEQ ID NO:2:

GAATGTATTA GAATGTAATG AACTTTA                                              27

(2) INFORMATION FOR SEQ ID NO:3:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (genomic)
              (A) DESCRIPTION: nucleic acid primer (iii) HYPOTHETICAL: NO (iv) ANTI-SENSE: NO (viii) POSITION IN GENOME:
              (A) CHROMOSOME/SEGMENT: Y chromosome
              (B) MAP POSITION: 3.4 kb Hae III repeat sequence (ix) FEATURE: Primer for sequence of Y chromosome
              (A) NAME/KEY: primer WYR5
              (C) IDENTIFICATION METHOD: by experiment (xi) SEQUENCE DESCRIPTION: SEQ ID NO:3:

GGAATCTAAT GGAATGGAAT TAAATGG                                              27

(2) INFORMATION FOR SEQ ID NO:4:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (genomic)
              (A) DESCRIPTION: nucleic acid primer (iii) HYPOTHETICAL: NO (iv) ANTI-SENSE: NO (viii) POSITION IN GENOME:
              (A) CHROMOSOME/SEGMENT: Y chromosome
              (B) MAP POSITION: 3.4 kb Hae III repeat sequence (ix) FEATURE: Primer for sequence of Y chromosome
              (A) NAME/KEY: primer WYR6
              (C) IDENTIFICATION METHOD: by experiment (x) PUBLICATION INFORMATION:
              (A) AUTHORS: Goonewardena, P.
                    Pletcher, B.A.
                    Pergolizzi, R.
                    Bowen, W.T.
              (B) TITLE: Use of PCR with Y-Specific Probes for Rapid

```
                Sex Determination
        (C) JOURNAL: American Journal of Human Genetics
        (D) VOLUME: 45
        (E) ISSUE: 4
        (F) PAGES: A190
        (G) DATE: 18-OCT-1990

(xi) SEQUENCE DESCRIPTION: SEQ ID NO:4:

TTCCATTCCA TTCCATTCCT TTCCTTT                                     27

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: nucleic acid primer (iii) HYPOTHETICAL: NO (iv) ANTI-SENSE: NO (viii) POSITION IN GENOME:
        (A) CHROMOSOME/SEGMENT: Y chromosome
        (B) MAP POSITION: 3.4 kb Hae III repeat sequence (ix) FEATURE: Primer for sequence of Y chromosome
        (A) NAME/KEY: primer WYR7
        (C) IDENTIFICATION METHOD: by experiment (x) PUBLICATION INFORMATION:
        (A) AUTHORS: Weier, Heinz-Ulrich G.
            Seagraves, Richard
            Pinkel, Daniel
            Gray, Joe W.
        (B) TITLE: Synthesis of Y Chromosome-Specific Labeled
            DNA Probes by In Vitro DNA Amplification
        (C) JOURNAL: Journal of Histochem. Cytochem.
        (D) VOLUME: 38
        (E) ISSUE: 3
        (F) PAGES: 421-426
        (G) DATE: 09-MAR-1990

(xi) SEQUENCE DESCRIPTION: SEQ ID NO:5:

TGGGCTGGAA TGGAAAGGAA TCGAAAC                                     27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: nucleic acid primer (iii) HYPOTHETICAL: NO (iv) ANTI-SENSE: NO (viii) POSITION IN GENOME:
        (A) CHROMOSOME/SEGMENT: Y chromosome
        (B) MAP POSITION: 3.4 kb Hae III repeat sequence (ix) FEATURE: Primer for sequence of Y chromosome
        (A) NAME/KEY: primer WYR8
        (C) IDENTIFICATION METHOD: by experiment (x) PUBLICATION INFORMATION:
        (A) AUTHORS: Weier, Heinz-Ulrich G.
            Seagraves, Richard
```

```
            Pinkel, Daniel
            Gray, Joe W.
      (B) TITLE: Synthesis of Y Chromosome-Specific Labeled
          DNA Probes by In Vitro DNA Amplification
      (C) JOURNAL: Journal Histochem. Cytochem.
      (D) VOLUME: 38
      (E) ISSUE: 3
      (F) PAGES: 421-426
      (G) DATE: 09-MAR-1990

(xi) SEQUENCE DESCRIPTION: SEQ ID NO:6:

TCCATTCGAT TCCATTTTTT TCGAGAA                                      27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: nucleic acid primer (iii) HYPOTHETICAL: NO (iv) ANTI-SENSE: NO (viii) POSITION IN GENOME:
        (A) CHROMOSOME/SEGMENT: Y chromosome
        (B) MAP POSITION: 3.4 kb Hae III repeat sequence (ix) FEATURE: Primer for sequence of Y chromosome
        (A) NAME/KEY: primer WYR9
        (C) IDENTIFICATION METHOD: by experiment (xi) SEQUENCE DESCRIPTION: SEQ ID NO:7:

ATGGAATTGA ATGGAACGGA ATAGAGT                                      27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: nucleic acid primer (iii) HYPOTHETICAL: NO (iv) ANTI-SENSE: NO (viii) POSITION IN GENOME:
        (A) CHROMOSOME/SEGMENT: Y chromosome
        (B) MAP POSITION: 3.4 kb Hae III repeat sequence (ix) FEATURE: Primer for sequence of Y chromosome
        (A) NAME/KEY: primer WYR10
        (C) IDENTIFICATION METHOD: by experiment (xi) SEQUENCE DESCRIPTION: SEQ ID NO:8:

CGATTCCATT CAATTCGAGA CCATTCT                                      27

(2) INFORMATION FOR SEQ ID NO:9:

(i) SEQUENCE CHARACTERISTICS:
        (A) LENGTH: 3564 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (x) PUBLICATION INFORMATION:
    (A) AUTHORS: Nakahori et al.
    (B) TITLE: A human Y-chromosome specific repeated DNA family
        (DYZa) consists of a tandem array of
        pentanucleotides
    (C) JOURNAL: Nucleic Acids Research
    (D) VOLUME: 14
    (E) ISSUE: 9
    (F) PAGES: 7569-7580
    (G) DATE: 1986

(xi) SEQUENCE DESCRIPTION: SEQ ID NO:9:

```
TTCCATTCCA TTCCAATCCA TTCCTTTCCT TTCGCTTGCA TTCCATTCTA TTCCCTTCTA      60
CTGCATACAA TTTCACTCCA TTCGTTCCCA TTCCATTCAA TTCCATTCCA TTCAATTCCA     120
TTCCATTTGT TTCCATTCTC TTCGATTCCA TTTCTTTATA TTCCATGCCA TTCGATTCCA     180
TTCTATTGGA TTGCATTACA TACGTGTTCA TTCCATTCCA GACCATTCCA TTTGACTCCA     240
TTCCTTTCGA GCCCTTTCAA TTTGAGTCCA TTCCTTTCCA GTCCATTTCA CTCCAGTCCA     300
TTACTATCCA TTCCATACCA TTCCATCCCA TTCCATTCCA TTCCATTCCA TTCCATTCCA     360
TTGCATTCCA TTCCATTCCA TTCCATTCCA TTCCATTCCA TTGCACTGCA CTCCATTCCA     420
TTACATTCTA CTCTATCTGA GTCGATTTTA TTGCATTAGA TTCTATTCCA TTGGATTACT     480
TTCCATTCGA TTACATTCCA TTCATGTACA TTCCATTCCA GTCAATTACA TTCGAGTTCA     540
TTACATTACA TTCCAGTATA TTCCATTGTA TTCGATCCCA TTCCTTTCAA TTCCATTTCA     600
TTCGACTCCA TTATATTCGA TTCCATTCCA CTCGAATCCA TTCCATTAGA GGACATTCCA     660
TTCCAATGCA TTCCATTCCA TTCCATAGCA TTCCATTGCA TTCGATTCCA TTCCATTTGA     720
TGCCATTCCA TTTGATGCCA TTCCATGACA TTCCATTCCA TTCGAGTCCG TTCCGTTCCA     780
ATTCATTGCA TTCCGTTTCA TGAAATTCGA GTCCTTTCCA GTACATTTCA TTCCAATCCC     840
ATCCAATCCA ATCTACTCCA TTCAATTCCT TTCCATTCCA TTTGATTTGA TTCCATTGAT     900
TTGATTCCAT TCAGTTTGAT TCCATTCCGT GAAATTTCGT TCCATTCTAT TCTATTACAT     960
AACTTTCCAT TCAATTCCAT TCCATTTCAT TTCAGTCCAT TCGCTTCCTT TCCTTTCGAT    1020
TCAATTCCAT TTGATTCCAC TCCATTCTAT GCAATTTCAT TCCAATCGAT TCAATTCCAT    1080
TCGATGACAT TCCTTTCGTT TCCATTCCAT TCGAGTCCAT TCAATTTGAG CATTCGTGTC    1140
CATTCTATTC GAGTCCATTC CATTACCGTC TATTCTATTC CCTTCCATTC CTGTTGATTC    1200
AATTTCATTC CCTTCCATTC GATTCCTTTC CATTCGATTC CATTCCTTTC CATTCCATTC    1260
CATTCGTTCC CATTCCATGT GATTTCATTC CATTCCAGTC CATTATATTC GAGTCCACTC    1320
CACTCCATTC TATTACATTC AATTCCTTTT GAGTCCGTTC CATAACACTC CATTCATTTC    1380
GATTCCATTT CTTGACAGTT TTCTTCCATT TTATTCCATT CCGTTCGATT CCATTCCATT    1440
CGATTGCATT CCATTCGAAT CCTTTCCATT CCATTTCATT CCATTCCTTT CTATTCCATT    1500
CCATTTCATT CGATTTGATT CCATTCTGTT CTATTCCATT CAATTCTTTT TCATTCCATT    1560
CGAATCCTTT CTATTGCAGT CCATTCCATT CGAGTCCATT CCAATCCCTT CCATTCCATT    1620
CCATTACAGT CCATTCCAAT AGATTCCATT CCTTTGCCTT CCATTCGAAT CCATTCCATT    1680
CTAGTCCATT CCATTTGAGT CAATTCCATT CCATTCCATT CTATTCCTTT CCAATCCATT    1740
CGATTCCATT CGATTCAATT CCATTTGATT CTCTTTCATT CTATTTTATT CCATGCCATT    1800
```

```
TTATTGCGTT GCATTCCATT CCGTTTGATT CCAGTCCATT CAAGAAAGTT CCATTCCAGT      1860

CCATTGCTTT CCAGTCCATT CCATTCCACT CTTGTCTATT CCACTCCATT CCTTTCCATT      1920

CCATTCCATA CTATTCCATT CCATTCCTTT GCATTCCGTT TCCAATCTAT TCGAGTCCAT      1980

TGCATTCCAG TCCAATCCAT TCCATTACAT TCCTTTTGGT TCCCTGCCAG TCGATTGCAT      2040

TGCATACTAG ACCATTCCAA ACCAGTCCAT TCCATTCTAT TTCAACACTT TCCATTCCAC      2100

TCTGTTCGAG TCCATTCCAT TCCAGTCCAT TTAATTCAAG GGCATTCCAT TCCATTCCAG      2160

TCCATTTCAT GTTATTCCAT TCCATTCAAT TCCATTCCAG ATGATTCCAT TCCATTCTAT      2220

ACCATTGCTC TCTGTTCCAT TCCATTCCAT CTGTCTCCAT TCCTTTCGTT TCGATTCCTT      2280

TCCATTCCAT TCCATTACAT TTGATCCTAT TTTATTAAAT TGCATTCTAT TCGAGTGATT      2340

TCCCTTCGAG TCCTTTCCAT TCAATTCCAT TCCATTCTAT TCCATTCCTT TGGATTCCAT      2400

TCCATTCCGT TCCGTTCACA TCAATTCCTT GTGATTCCAT TACATTCGAT TTCTTGCCAT      2460

TCGATTCCAT TCCTTTTGAC TCCATTTCAT TCGATTCCAT TCCATTCCAT TAATTTCCAT      2520

TCCATTCGAG ACCTTTCCAT TGCAGTCTTT TCCCTTCGAG TCCATTCCGT TCGATTCCCT      2580

TCCATTCGAT TCCATTCCAT TGGAGTCCGT ACCAGTCGAG TCCATTCTAT TCCAGTCCAT      2640

TAGTTTCGAC TCCATTGCAT TCGAGTGCAT TCCATTCCGT GGTTGTCCAT TCCATTCCGT      2700

TTGATGCCAT TCCATACGAT TCCATTCAAT TCGAGACCAT TCTATTCCTG TCCATTCCTT      2760

GTGGTTCGAT TCCATTTCAC TCTAGTCCAT TCCATTCCAT TCAATTCCAT TCGACTCTAT      2820

TCCGTTCCAT TCAATTCCAT TCCATTCGAT TCCATTTTTT TCGAGAACCT TCCATTACAC      2880

TCCCTTCCAT TCCAGTGCAT TCCATTCCAG TCTCTTCAGT TCGATTCCAT TCCATTCGTT      2940

TCGATTCCTT TCCATTCCAG CCCATTCCAT TCCATTCCAT TCCTTTCCTT TCCGTTTCAT      3000

TAGATTCCAT TGCATTCGAT TCCATTCAAT TCAATTCCGT GCTATTCAAT TTGATTCATT      3060

TCCATTTAAT TCCATTCCAT TAGATTCCAT TCCGTACGAT TCCATTCCTT TTGAATCCAT      3120

TCCATTGGAG TCCATTCACT TCCAGAACAT TCCATTCCAG TCGAATCCAT TCGAGTACAT      3180

ACCATTAAAG TTCATTACAT TCTAATACAT TCCATTCCAT TGCATTCCAT TCCATTCCAT      3240

TAGATGCCAT TCGATTCCAT TCCATGCCAA ATCATTGCAT TCCTTTCCAT TCCGTTCCTA      3300

TCAATTCTAT TCCATTCGAT TTAGTTCGAT TCTATTCACT TCCATTCCAT TCGATTCCAG      3360

TCCATTGGAG TCAATTCCTT TCGACACCCA GCCTTTCCAG TCAATGATTT TGGATTCCAT      3420

TTTTTTGCAT TCCATTACAT TCTATGACAT TCGATTCCGT TTCATTGCAT TCCATTCCAT      3480

ACATTTTTAT TCCATTCGAG ACCGTAGCAT TCCACTTTAT TCCAGGCCTG TCCATTACAC      3540

TACATTCCCT TCCATTCCAA TGAA                                            3564
```

(2) INFORMATION FOR SEQ ID NO:10:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
TTCCATTCCA TTCCATTCCT TTCCTTTCCG TTTCATTAGA TTCCATTGCA TTCGATTCCA        60
```

```
TTCAATTCAA TTCCGTGCTA TTCAATTTGA TTCATTTCCA TTTAATTCCA TTCCATTAGA      120

TTCCATTCCG TACGATTCCA TTCCTTTTGA ATCCATTCCA TTGGAGTCCA TTCACTTCCA      180

GAACATTCCA TTCCAGTCGA ATCCATTCGA GTACATACCA TTAAAGTTCA TTACATTCTA      240

ATACATTC                                                               248

(2) INFORMATION FOR SEQ ID NO:11:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TTCCATTCCA TTCCATTCCT TTCCTTTCCG TTTCATTAGA TTCCATTGCA TTCGATTCCA       60

TTCAATTCAA TTCCGTGCTA TTCAATTTGA TTCATTTCCA TTTAATTCCA TTCCATTAGA      120

TTCC                                                                   124

(2) INFORMATION FOR SEQ ID NO:12:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

ATTCCGTACG ATTCCATTCC TTTTGAATCC ATTCCATTGG AGTCCATTCA CTTCCAGAAC       60

ATTCCATTCC AGTCGAATCC ATTCGAGTAC ATACCATTAA AGTTCATTAC ATTCTAATAC      120

ATTC                                                                   124
```

Y CHROMOSOME SPECIFIC NUCLEIC ACID PROBE AND METHOD FOR DETERMINING THE Y CHROMOSOME IN SITU

This is a continuation of application Ser. No. 08/546,452, filed Oct. 6, 1995, now U.S. Pat. No. 5,888,730 which is a division of application Ser. No. 07/594,921, filed Oct. 10, 1990, now U.S. Pat. No. 5,840,482.

The United States Government has rights in this invention pursuant to Contract No. W-7405-ENG-48 between the United States Department of Energy and the University of California for the operation of Lawrence Livermore National Laboratory.

This application is related to a United States patent application entitled "PCR Method of Diagnosis of Fetal Gender from Maternal Blood" filed simultaneously with the present application.

BACKGROUND OF THE INVENTION

Y-Chromosome Determination

Over the years a number of methods have been developed for making a determination either directly or indirectly of the presence of the Y chromosome in a particular tissue sample.

Barr Body Test. The barr body test is an indirect method for determining that an XY karyology may be present in a tissue sample. Buckle smear and other tissue samples dyed with Giemsa reagent stain reveal the presence of any X chromosomes beyond one copy per cell. These chromosomes appear as barr bodies within the cell nucleus.

Unfortunately, the buckle smear method is not always accurate in predicting the presence of a Y chromosome. For instance, an XO genotype would give the same results as an XY genotype. Also, at various stages in the cell growth and division cycle or in certain tissue samples, barr bodies fail to become visible. Therefore, barr body testing is generally limited to non-critical screening assays.

Because of the limitations of barr body analysis, this method is not appropriate for use in invasively sampled fetal cells, such as chorionic villi or amniocentesis samples. The invasive sampling techniques used are expensive and not without risks. Therefore, multiple sampling is generally unacceptable, as are delays in re-diagnosis which can occur when test results are equivocal. Even a low level of false diagnosis is unacceptable in situations where prenatal gender would be the basis of pregnancy termination.

Karyology. With the advent of tissue culture techniques, direct karyology of cells became possible. However, there are several limitations to this technique. The sample tissue must be in an active growth phase during analysis to be useful in karyology. This is because the sample cells must be dividing for the chromosomes to be arrested in their condensed, visible metaphase stage.

In the case of mammalian tissue sample growth systems such as are required in conventional human prenatal diagnosis, karyology techniques have proven to be time consuming and expensive. Mammalian cell lines are highly fastidious in their culturing parameters and cell media requirements. Further, any contamination of mammalian tissue culture material can result in complete failure of growth of the cells.

Nucleic Acid Probes

The recent development of relatively Y specific DNA probes has great potential for many clinical, animal husbandry, forensic and paleontological applications, among other uses. Small or deteriorated tissue samples can be analyzed as long as a minimal amount of DNA can be obtained. If linked with the PCR or other amplification technologies, such probes are potentially useful in forensic determinations. In suspected rape cases, the presence of severely decayed sperm or its genetic remnants might be detected by such methods. Hair and fragmentary tissue samples could also be typed for gender. A very small sample size might be largely conserved by this method allowing a large amount of sample material for other analytical work.

Forensic Science Uses. PCR and DNA probes have been used in recent efforts to genetically identify highly decayed remains of "the disappeared" in Argentina and match children born in prison with remaining family members. Using a Y probe as an initial screening tool in such work or related work is useful in conserving limited samples.

Gender Determination Uses. Y probes are also potentially useful in determining the sex of embryos for transplant if only a single sex is desired, such as in various animal husbandry uses. When combined with artificial fertilization, such techniques could be used to increase the desired gender of offspring by subjecting sperm samples to column or other elusion techniques in order to enrich the sample for Y or X bearing sperm. For instance, Y bearing sperm can be bound to a labeled probe, and then sorted for gender. The Y or X bearing sperm can be collected, and utilized for insemination when male or female offspring are desired.

Presently Available Probes. The applicability of the presently available Y DNA probes are limited because the probes are only relatively Y chromosome specific. These probes have a comparatively high level of nonspecific binding to other chromosomes. This lack of specificity is believed to be due in part to the large size and complexity of the binding sequence employed in such probes. This nonspecific binding often varies from sample to sample, and so has an unpredictable impact on the sensitivity of the test in any particular situation.

In testing situations where the amount of Y chromosomal material is high compared to that of the other genomic DNA, the nonspecific binding inherent in prior art DNA Y probe systems is generally not critical to the success of the analysis. However, in other testing environments, the nonspecific binding of the probes results in the limitation of the applicability of the assay, or even forecloses its workability altogether. As an example, in the case of seeking Y chromosome bearing fetal cells in maternal blood, conventional DNA probes are ineffective. This is because conventional Y probes non-specifically bind to a high proportion of maternal genomic DNA. The signal from this non-specific binding obscures the signal from the binding to the very minute proportion of fetal DNA in the maternal blood.

There is a recognized need for probes with the capacity to bind exclusively to the Y chromosome. Presently available Y chromosome nucleic acid probe systems could be substantially improved by substituting such specific probes for the conventional probes now being employed. A technique by which a variety of such highly specific Y probes could be produced would allow a further improvement of these analytical systems. With such a technique, the most appropriate probe for any particular application could be developed.

Y chromosome specific nucleic acid probes made up of multiple copies of Y specific sequences would also have a number of advantages over the probes of the prior art. Probes of any particularly advantageous size could be manufactured. Additionally, substantial degradation of the probe's hybridizing nucleic acid strand could be suffered without loosing a large portion of the probe's annealing capacity.

Currently, there are no RNA probes for Y chromosome specific RNA products. However, such probes would be very useful for investigation of Y chromosome specific gene expression.

Polymerase Chain Reaction. In the past, DNA probes had limited applicability when the sample size of the target DNA was below detectable levels for a particular probe system. Detection of low sample sizes can now be accomplished by amplifying the desired sequence using polymerase chain reaction (PCR) techniques developed by various researchers (Mary, "Multiplying Genes by Leaps and Bounds," *Science*, Vol. 340, pp. 1408–1410, 1988). Such techniques have been used successfully in other areas of prenatal diagnosis such as in sickle cell anemia (Saiki et al., "Enzymatic Amplification of Beta-globin Genomic Sequences and Restriction Site Analysis for Diagnose of Sickle Cell Anemia," *Science*, Vol. 230, pp. 1350–1354, 1988). In the prenatal diagnosis materials successfully employed at present, the determination is one of relative levels of a DNA sequence in fetal cells in the presence of a small number of maternal cells. Materials are obtained through amniocentesis or chorionic villus sampling.

Prenatal Diagnosis of Fetal Gender

There are many clinical and social reasons for testing for fetal gender. There are a variety of clinical reasons for conducting such tests. It is useful to determine the sex of the fetus when there is a family history of sex-linked genetic diseases such as hemophilia. Gender determination would be helpful in such cases when planning neonatal and prenatal care and when making decisions concerning possible pregnancy termination. Such a diagnostic tool would be useful when there is a family history of such sex-linked genetic diseases as Lesch-Nyhan syndrome, Fabry disease, Hunter syndrome, Duchenne muscular dystrophy, nephrogenic diabetes insipidus, and glucose-6-phosphate dehydrogenase deficiency, among others.

There are other clinical applications of prenatal sex determination. Fetal gender determination is helpful to neonatologists and obstetricians in making judgments as to what treatment regimens are appropriate in particular cases. Gender determination can be a valuable clinical tool because of the greater maturity and survivability of female fetuses as compared to male fetuses of the same size and gestational age. For instance, fetal gender determination is useful when timing labor induction for fetal distress or for other reasons. It is helpful to have determined fetal gender when deciding to allow pre-term labor to proceed. Fetal gender identification can figure into an evaluation for potential lung maturation problems or other post-term risks.

Prenatal sex determination is important information for families with a strong gender preference. This is particularly true in countries where opportunities for women are very limited, and infanticide of female newborns is both historically and contemporarily practiced. Such practices could be dramatically diminished if early fetal sex determination were available with the option for a first trimester abortion.

Presently available techniques for fetal sex determination have a number of drawbacks which severely limit their use. These techniques are often suitable only for the later stages of pregnancy. They also require direct sampling of fetal tissues through cell collection from the amniotic fluid or the chorionic villus. Some success in fetal gender determination has been achieved by visualization of the fetus with ultrasound. Efforts have been made to test increased testosterone levels in the maternal blood as an indicator of fetal gender, but the results of this area of research have been inconclusive.

Amniocentesis. The advent and standardization of the amniocentesis procedure has resulted in the development of the now well established tissue culture technique for the analyses of fetal chromosomes. In this method, fetal lung and epidermal cells which have sluffed off into the amniotic fluid are sampled by the use of a large gauge hollow needle and a syringe. The cells are grown employing mammalian tissues culture techniques. Once sufficient growth is accomplished, the dividing cells are trapped in metaphase by the use of the spindle fiber poison colcemid. The resulting metaphase cells cultures are subsequently fixed, mounted, stained and photographed. Karyology, that is identification and grouping of the chromosomes, is then required to determine the sex of the fetus.

The amniocentesis method of gender determination has several drawbacks. Because there is no known treatment for most of the genetic diseases being tested for, the pregnancies in which affected individuals are predicted are often terminated. However, the test can only be accomplished in the second trimester of pregnancy due to lack of sufficiently developed fetal cells in the amniotic fluid in the earlier stages of fetal development. Pregnancy termination is considerably more complex at this stage, requiring more intervention, and with a greater risk of morbidity and mortality to the mother. Additionally, there are considerably more emotional problems to the family when pregnancies are terminated so late in the gestational period.

Although amniotic fluid sampling has been widely practiced with minimal complications, some degree of infection and other sequela have been associated with this sampling method. The expense of the diagnostic procedure is considerable, in part because eucaryotic cell culture techniques must be used for sample processing. The techniques require special laboratory facilities. Also, the cell culturing procedure requires considerable amounts of the time of skilled laboratory personnel to be reliably successful.

If the cultures of fetal cells become contaminated or fail to grow in some other way, the amniocentesis sampling procedure must be repeated. This can result in time delays which can put the pregnancy beyond the allowable period for a therapeutic abortion.

Because of the expense and complexity of this testing method, amniocentesis with cell culture and karyology is not available as a general screening tool. Candidates for the procedure often must journey to large metropolitan areas to have the test done. Screening for gender preference reasons is routinely denied to families because of the limited availability of the procedure, and the number of medically necessary cases requiring this limited resources. The entire process requires several weeks to obtain the needed information and generally costs over $500. Thus, this method is not useful in many of the other clinical situations enumerated above. Karyology and thus much of the expense and time cost of this procedure could be eliminated by the use of a reliable Y probe with a strong signal.

Chorionic Villi Sampling. A new prenatal diagnostic technique using the sampling of chorionic villus has been recently introduced. Although there is an increased risk of miscarriage from the procedure as compared to standard amniocentesis sampling techniques, chorionic villus sampling allows testing in a somewhat earlier stage of the pregnancy.

Unfortunately, the expense and commitment of laboratory staff and facilities to sample processing required by chorionic villus analysis is similar to the well established amniocentesis method. As with the amniocentesis sampling method, facilities equipped to process the samples are virtually unavailable to third world countries. The transport of the samples to appropriate testing centers is prohibitively expensive. Sadly, the countries which cannot provide such services are also those suffering from some of the highest rates of infanticide. As with amnio center is, such of the expense and waiting period required in this method could be eliminated by the use of a reliable Y probe with a strong signal.

Ultrasound Diagnosis. With the advent of ultrasound techniques in obstetrical practice, the gender determination of fetuses in late pregnancy has become a standard event in many pregnancies. However, relying on such visualizations as the basis for pregnancy termination is not standard medical practice. Even in the newborn infant, sex determination by physical observation can be highly variable due to a number of different factors such as localized edema. Additionally, as is the case with amniocentesis and chorionic villus sampling, the determination is made very late in the pregnancy with all of the incumbent disadvantages and even outright legal bars to pregnancy termination.

In certain academic radiology departments, there have been some claims that fetal gender can be determined by ultrasound methods as early as 11 weeks of gestation. However, it is generally accepted that such determinations cannot be reliably made before 16 gestational weeks even in an academic setting with state of the art equipment and a highly skilled radiologist making the determination. Even after 16 weeks gestational age, false determinations of female gender are possible.

DNA Probes. Some advances in the detection of Y chromosomal DNA have been made in the last few years by the use of DNA probes which display homology to various regions of the Y chromosome. However, none have been applied to the prenatal determination of gender with the possible exception of direct assays of fetal tissue as described above.

Prior art techniques for producing Y "specific" DNA probes are applicable only to testing requirements that allow some homology and binding of the probe to certain autosomal and X sequences. Thus, these prior art probe sequences have proven to be Y preferring rather than truly Y specific. RNA probes specific for Y chromosomal products have not been developed at all.

The conventional Y DNA probes preference binding is appropriate and workable where there is no significant degradation of the test material, and large amounts of Y containing DNA material are present. For instance, such tests would be applicable to making determinations of testicular feminization or other sex chromosome anomalies in children and adults. However, as a practical matter, such a role is filled by the inexpensive barr body test using a standard Giemsa reagent stain to identify a second X chromosome in fixed cells.

Where a sample of fetal tissue is taken directly from the amniotic fluid in the form of discarded epithelial cells, or where a portion of the chorionic villus is sampled, these new probes may potentially provide a method of determining fetal gender without resorting to expensive, time consuming cell culture or karyology technique, or as a confirmation to a borderline barr body test.

SUMMARY OF THE INVENTION

It is an object of the present invention to provide a method of identifying and producing nucleic acid probes, some portion of said nucleic acid being capable of binding exclusively to the Y chromosome or its tRNA transcription.

It is another object of the present invention to provide a nucleic acid probe of such sensitivity and specificity that it can accurately detect Y-chromosomal nucleic acids in the presence of a large amount of autosomal and X chromosomal nucleic acids such as a sample of fetal cells.

It is yet another object of the present invention to provide a nucleic acid probe of such specificity that it can detect a very small amount of Y chromosomal nucleic acids even when these nucleic acids have suffered substantial degradation and are present with large amounts of autosomal and X nucleic acids, such as in forensic testing.

It is an additional object of the present invention to improve prior art nucleic acid probes by substituting for or augmenting the binding sequences of such probes with the inventive highly Y specific DNA segments or RNA sequences It is another object of the present invention to provide a probe of a highly repeated sequence on the Y chromosome which, because of its high copy number, produces a strong signal, and can be used for chromosome enumeration in interphase cells, sperm, and chromosome studies in metaphase cells.

It is yet another object of the present invention to provide a probe which is useful in following the success of bone-marrow transplants, in detecting tumors, and in biological dosimetry uses.

It is another object of the present invention to use primers specific for Y chromosome exclusive nucleic acid sequence singly or paired with primers at relatively distant positions on the Y chromosome to produce nucleic acid sequences suitable for Y chromosome painting or decorating in order to observe such modifications as translocations or deletions.

It is yet another object of the present invention to provide Y chromosome tRNA product specific RNA.

Probe Sequence Development

A method has been developed for producing Y chromosome specific probes which have very limited nonspecific binding to other chromosomes and/or their RNA transcription products. The use and production of these new probes can be extended by optionally using an amplification technique such as PCR for the nucleic acid probe and/or the nucleic acid sample to be tested. PCR can also be used to amplify cDNA templates for RNA probe production. The present invention avoids the limitations of the prior art Y probes by providing a probe that is truly Y specific, with minimal or no binding to the autosomal and X chromosomes and/or chromosomal products even at extremely high copy levels and with many amplification steps.

In cases where the percentage of male cells is very small or in various stages of degeneration, considerable amplification is often employed in order to increase the sample Y nucleic acid levels which can be detected within the sensitivity limits of the assay. An example of such a method is set forth is sister case Ser. No. 07/594,922. When RNA is being analyzed, a transcription initiation step may be included. In these testing situations, cross reactivity to autosomal and X chromosomal DNA or RNA becomes a significant factor in the design of the method.

During the inventors' research efforts in systems requiring high specificity of probe binding, it has become apparent that prior art Y probes have a high level of cross reactivity to non-Y chromosomal material and chromosomal RNA product that reduces their utility in many systems where the test samples includes large amounts of non-Y chromosomal nucleic acid. For instance, prior art Y probes are ineffective in the determination of fetal gender from maternal blood samples and for many forensic and paleontological assay requirements. The present inventive probes and assay methods avoid these limitations of the prior art probes and assay methods.

The inventive probes are also highly suitable for use in existing, less rigorous assay systems. Their lack of cross-reactivity would allow them to be employed in some cases for a reduced cost in existing assay systems due to their higher specificity. The relatively small size of the inventive probes would allow for cheaper production cost and a wider range of appropriate vectors and labels as compared to prior art probes. Additionally, the inventive probes could suffer degradation but still maintain their effectiveness as a feature of their high redundancy. This would give the inventive probes a longer shelf life and wider range of handling and storage as compared to prior art probes.

The probes of the subject invention may be labeled in any of the conventional manners, such as with specific reporter molecules, (biotin, digoxygenin, etc.), fluorescent chemicals, radioactive materials, or enzymes such as peroxidases and phosphatases. Double labeling can also be employed. A preferred method particularly suited to the present invention is labeling by biotinylation during amplification or other production methods. This preferred method is described below in Example 1.

Use of PCR and Development of PCR Primers

Depending on the application, amplification may be useful in achieving desired goals in the production and use of the inventive probes such as in the sister case, Ser. No. 07/954,922. For instance, the nucleic acid sequences which bind to nucleic acid of the Y chromosome of the present invention may be highly amplified before being used as Y chromosome probes. When RNA is to be tested, the cDNA serving as its template can be advantageously amplified by PCR. Additionally, the Y specific sequences of the test material can be highly amplified using the inventive techniques and primers of the subject invention. This either allows an increase in DNA for direct sampling, or gives a larger transcription base for RNA to be tested. Such amplification techniques may be minimized or excluded all together when the Y chromosomal nucleic acid to be tested for is present in the sample at sufficiently high levels, or when samples can be enriched for the target nucleic acid.

PCR amplification techniques provide some advantages in producing large numbers of probes without the time and expenses required by some cloning or other production methods. However, one could always use these more conventional methods of nucleic acid replication for any of various reasons. In some cases, such as mass production in a fermentation type situation, conventional amplification techniques might be preferable to PCR methods.

A method for identifying and tailoring Y repeat specific DNA primers to specific needs has been developed. When the desired Y specific sequence is identified, primers are chosen which flank this region. The use of such carefully selected primers allows the amplification of a limited, desired region of the Y chromosomal nucleic acid. This high specificity avoids replication of sequences which are non-specific in their binding. It also increases the productivity of the replication operation. This method can be expanded to provide a large DNA template base for the production of tailor made RNA probes. The initial cDNA may be produced from mRNA by reverse transcription.

Primers as describe in sister case serial Ser. No. 07/594,922, allow specific amplification of the DNA target region in a test sample where the region is known to exist at a very low level prior to testing. It provides for one of several methods for producing large numbers of probe copies. Such primers can also serve as the basis for a test where a resultant high level of nucleic add production indicates the presence of the target sequence.

The primers described herein have uses distinct from the inventive prenatal diagnosis method. Primers can be chosen which are some distance from one another on the highly repeated region of the Y chromosome. The DNA product from such a pairing in a PCR amplification procedure would be useful in Y chromosome painting or decoration efforts. This type of product when bound to an appropriate label is useful in observing deletions or translocations. Long arm crossing over of the chromosome will be readily observed by these products because the sequences are in the distal arm region of the chromosome. A number of the DNA products produced in this manner can be used in concert to produce a more complete painted effect.

Labeled RNA probes produced by the present method would be useful in demonstrating transcription rates and also in locating the position in the cell where transcription is occurring.

BRIEF DESCRIPTION OF THE DRAWINGS

The file of this patent contains two color photographs. Copies of this patent with color photographs will be provided by the Patent and Trademark Office upon request and payment of the necessary fee.

FIG. 1—is a nucleotide map of a typical highly repeated sequence of the Y chromosome used for selecting appropriate probe sequences.

FIG. 3—is a complete nucleic acid map of various examples of the inventive primers.

DETAILED DESCRIPTION OF THE INVENTION

Probe Identification and Manufacture

The present invention allows the identification of appropriate nucleic acid sequences which can serve as recognition sequences on nucleic acid probes for the Y chromosome. These inventive probes display little or no nonspecific binding to autosomal and X chromosomes and their RNA products. The nonspecific binding of the probes of the present invention is generally less than $10^{-4}$. The nonspecific binding can range from $10^{-2}$ to $10^{-7}$, preferably $10^{-3}$ to $10^{-6}$, and most preferably $10^{-4}$ to $10^{-5}$. The level of nonspecific binding of a selected sequence is tolerated based on the requirements of the particular system for which the probes are being developed, and counterbalancing positive aspects of any particular probe sequence.

Figure 6A:
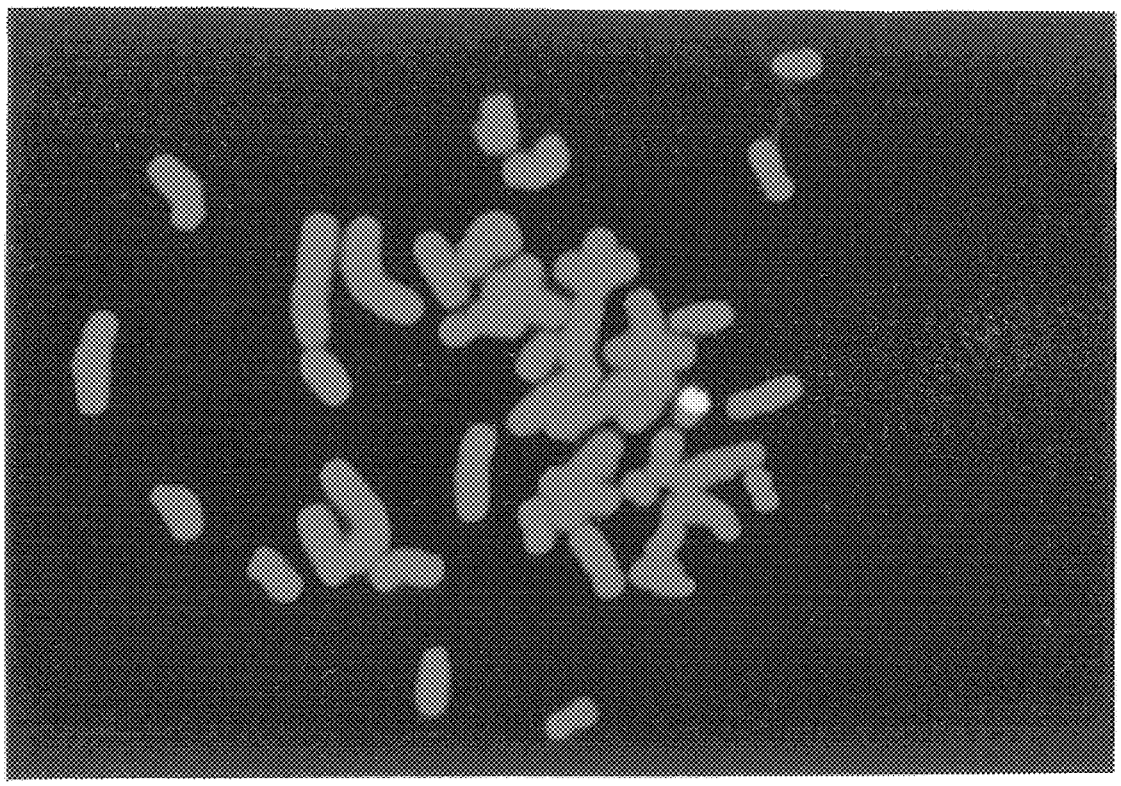
FIG. 6(a)—shows the result of the inventive labeled probe binding in the metaphase and interphase stages of cell division in blood from male volunteers.

The inventive Y probe sequences are preferably derived from repetitive sequence regions on the Y chromosome. Some of the repetitive sequence regions are located on the long arms of the chromosome, as is demonstrated in the examples below and as can be seen in FIG. 6(a). The inventors have discovered that choosing slightly less repetitive sequence from among these large groups of highly repetitive sequences of the Y chromosome is most likely to produce a probe with good specificity and other binding qualities. However, that strategy must be tempered by the understanding that base pair sequences homologous with autosomal and X sequences are interspersed in the highly repetitive regions of the Y chromosome. Therefore, it is more advantageous in some cases to select relatively short minimally repetitive sequences within a repetitive region as candidates for probes of the inventive type.

Some Y chromosome regions which are highly repetitive have been described in the literature. Nakahori et al. provided a description of a 3.4 kilobase pairs (kb) repeated sequence (*Nucleic Acids Research* Vol. 14, No. 19, 1986). Smith et al. reported on a 2.6 kb repeated sequence (*Developments* 101 Supplemental pp. 77–92, 1987). One such large map of the 3.4 kb Hae III repeat is provided as FIG. 1. Some of the probe candidates investigated by the inventors were selected as portions from this large nucleotide sequence base pair (bp) map and are provided in FIGS. 2–4.

Using the inventive method, a large variety and number of Y chromosome specific probes can be developed. The sequences of a number of likely probes are selected. The best choice for a specific purpose is identified from among a number of these selected sequences. These identified probes can then be synthesized by any one of several appropriate methods. As can be seen from the examples below, the size of the fragment which is selected is not critical to its having Y specific characteristics. The size of these probes can be from 8–600 bp in length. Within this large range, 8–250 bp will be the usual range, 8–100 bp the average range, a preferable range will be 8–75 bp, and the most preferred range is 8–30 bp.

The length of the candidate probe sequence can be chosen with a view towards the intended function of the final probe and its diagnostic environment. Alternatively, large probes can be chosen, and then the size narrowed. As the size is diminished, further testing is required to assure that the smaller conserved sequence still maintains sufficient hybridization capacity to fit a particular need.

Some of the isolated fragments chosen as probe candidates will have a higher binding affinity than others. The identity of these particularly advantageous sequences can be determined through simple screening procedures. One such procedure is to label the test probe, incubate it with a fixed and denatured metaphase cell, and observe its binding pattern as described below. Alternatively, when an RNA probe is employed, binding to RNA products is observed. Another procedure is to observe the probes by separation using gel electrophoresis as shown in Example 1 below. A most preferred method would be to utilize the classic Southern Blot method to find adhesion to the Y chromosome or to the repetitive sequence. (Maniatis et al., *Molecular Cloning: a Laboratory Manual*, Cold Spring Harbor, Cold Spring Harbor Laboratory, 1986).

Figure 2:
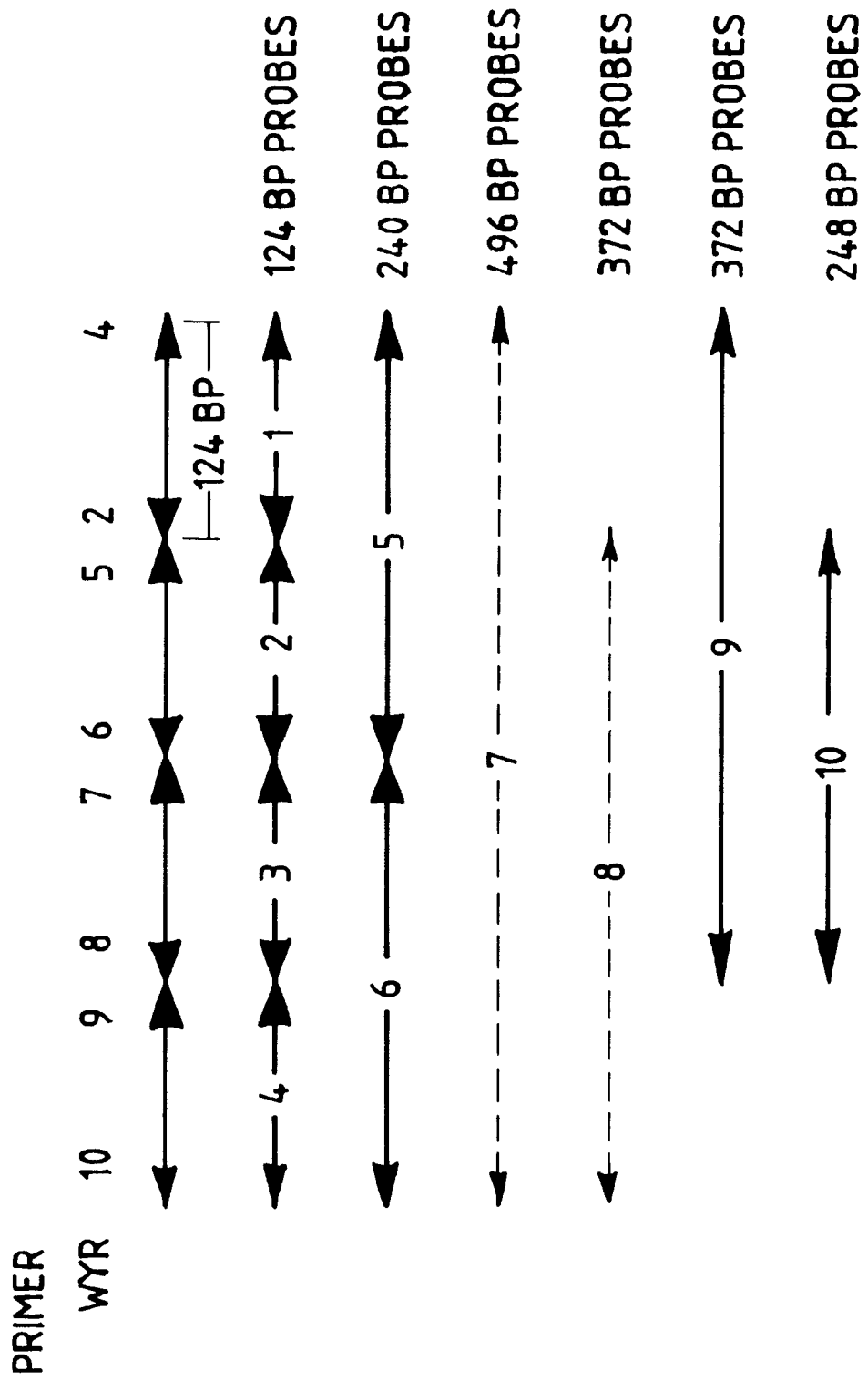
FIG. 2—is a map of a portion of the highly repeated sequence of FIG. 1, showing the position of some examples of the inventive probe, flanked by inventive primers which are indicated by number, from Nakahori et al., Nucl. Acids Res., Vol. 14, pp.7569–80, 1986.

The inventors have constructed DNA probes from highly Y specific sequences identified and produced by the inventive method. Several of these DNA probes are shown in FIG. 2. Their RNA counterparts can be produced when RNA probes are preferable. Combinations and rearrangements of these probes and probe fragments either sequentially or in repeats can provide for effective probes. Promoter and restriction sites are also useful additions to the probes for cloning and other purposes, and do not diminish the usefulness of the resulting product. These multiple approaches of the inventive concept allow the production of probes specifically designed to be optimally suitable for particular production methods or applications of the end product.

The probes developed by the above method are useful for improving present assay methods. This can be done by substituting the small, highly specific inventive probes for the conventional probes employed in prior art methods. Additionally, the probe isolation and manufacture method of the present invention allows great flexibility in custom designing probes to meet particular requirements. In some cases, it may be advantageous to produce probes of a very large size, say well over the 400 bp probes suggested above.

PCR Primers and Techniques

The applications of the inventive probes can be augmented using PCR technology. The development and mass production of the inventive DNA probe sequences can also be accomplished using PCR and can provide a large DNA template pool for the production of RNA probes. PCR technology allows amplification of the DNA probe and DNA template for RNA probe production without employing conventional cloning methods. Alternatively, PCR can be used as an adjunct to conventional DNA cloning methods. For instance, PCR can be effectively used to provide an initial amplifying step prior to other cloning methods. Because of the specificity of the probes produced by the method of the invention, PCR can be used to preferentially amplify the Y specific nucleic acid sequence in sample fractions to be tested in order to increase the sensitivity of the test.

To achieve this advantageous amplification of the inventive DNA probes and templates by PCR techniques, an appropriate primer sequence must be identified. Probes can be identified and synthesized using primers which bind to the highly repeated nucleic acid sequences of the Y chromosome. Examples of such primers developed by the inventors are shown in FIG. 3. Several of the many uses of the inventive primers are demonstrated in the Examples below.

The basic requirement for DNA primer candidates is that they be homologous to an appropriate stretch of the base pair sequence flanking the desired probe sequence. They can include base pair sequences in common with the probe, and may also extend away from it in either direction as much as is useful to the needs of specificity and other considerations.

In some cases in the present invention, a single primer can serve both as the first and bracketing primer. This phenomena is due to the highly repeated characteristics of the area of the Y chromosome being amplified. For instance, the recognition sequence of the primer can also occur on the opposing strand as an inverted repeat sequence. Thus no "second" primer is required in that case to allow efficient PCR.

Figure 4:
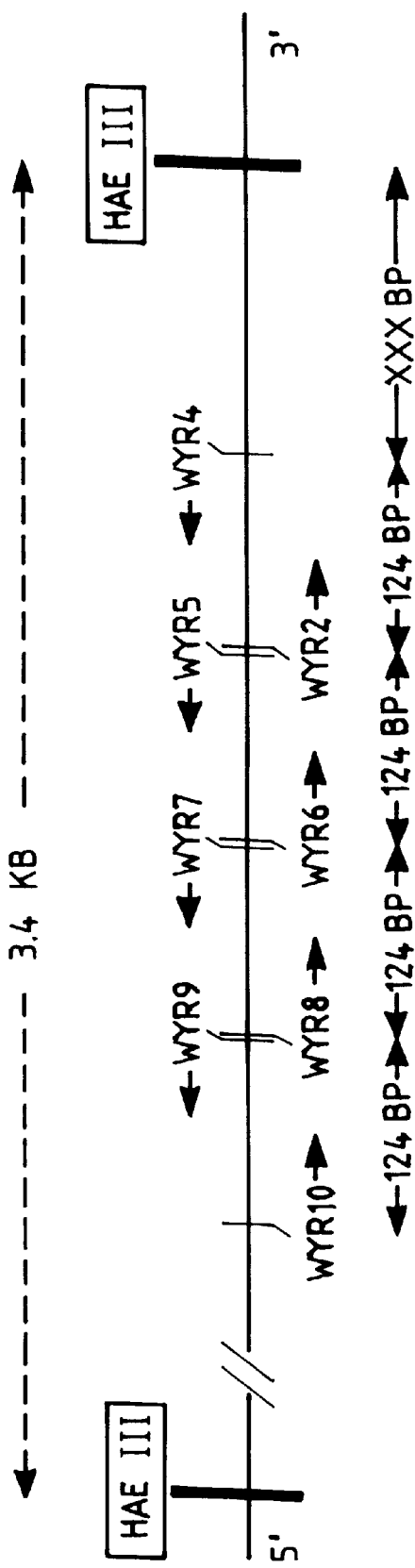
FIG. 4—is a map of the inventive PCR primers within the 3.4 kb repeat sequence.

In the examples provided below, primer sequences were chosen which flank the desired probe sequence. This arrangement of some of the inventive probes is seen in FIGS. 2 and 4. Typically, the primers were included within the desired probe sequence in order to avoid the requirement for separation and to maximize the production of the desired probe sequence. The primers may be from 5 to 100 bp in length. In the case of very small sizes, annealing must be accomplished at low temperatures, often as low as 4° C. A preferable range of sizes for primers is 10–53 bp. The most preferred range is 15–30 bp primer length.

In choosing a primer, it is best to select a sequence which will not bind to other areas of the Y chromosome or to RNA transcribed on other areas of the Y chromosome. Furthermore, it should not bind to autosomal sequences or X chromosomal sequences. When a primer does bind to non-selected sequences, a number of complicating phenomena occur. The resulting product is contaminated by undesirable sequences. These sequences tend to be much longer than the desired sequences because they are not flanked by a primer reading in the opposite direction on the homologous strand.

Non-target polymerization also causes a competitive use of the pool of substrate enzymes and other reactant material. This non-target polymerization compromises the efficient amplification of the desired sequence. Further, the resulting pool of nucleic acid fragments is likely to be highly contaminated with undesirable sequences.

The sequences of interest are in a highly repetitive area of the chromosome. This is a particularly complicating factor in the present inventive process because there may be non-target binding at some other portion of the repetitive region. Often, simply starting the primer sequence a nucleotide or two upstream or downstream from the first primer candidate will serve to ameliorate non-target binding. Much of this analysis can take place prior to any actual synthesis or testing by manual or computer search of the bp map of the repetitive region. This mental step saves considerable time and effort in the primer identification process.

As in the examples below, the annealing sites of primers WYR2 and WYR4 within the 3.4 kb repeat are chosen to have a minimum of deviation from the human satellite III DNA pentameric repeat motif TTCCA. These primers are considered to have a sequence eccentric to the other sequences found in the highly repeated region. This deviation is caused by single base pair changes in the consensus repeat motif. In the examples below, the first pair of primer sites was selected flanking the Rsal site at position 3177. For a given primer length of 27 nucleotides, the chances of partial annealing, i.e. the binding of the primer to the DNA template with some base pair mismatches, was investigated for primer annealing sites 1 to 5 bases 3' and 5' from the first selected sequence. Primer annealing sites with a minimum of matching bases, when annealed to other parts of the repeat, were finally chosen. The resulting distance of the 5' ends of the primers of choice was 124 bp. An additional pair of primers were synthesized to anneal in a distance of 124 bp or multiples thereof.

During preliminary experiments it became obvious that some of the additional primers chosen did not have as high a specificity for Y chromosomal DNA as other inventive primers. These individual less specific primers can be used in concert with highly specific primers using PCR amplification for diagnostic purposes. The successful generation of target DNA products that appear in the expected size range depends on both primers annealing at the correct distance from one another along the DNA template. In such reactions, multiple annealing of the less specific primer at various non-target sites does not result in the generation of a significant amount of DNA fragments in the expected size interval. Thus, the presence of secondary annealing sites for the second primer molecule in PCR does not necessarily compromise detection sensitivity. In most applications, pairs of either two highly specific or one highly specific primer combined with a less specific primer may give the same or comparable assay results.

The situation is different when both primer molecules find secondary annealing sites at the same spacing distance and orientation as the target sites. Although the primer pairs show amplification of DNA in the target size interval in samples containing only female DNA, certain primer combinations with reduced specificity find applications in samples containing a higher fraction of male cells.

An example for such a primer pair is the combination WYR2 and WYR4. After 20 PCR cycles, a strong band in the target size interval was observed in samples containing at least 1% male cells. Samples of female cells, on the other hand, did not show DNA fragments when aliquots of the PCR reaction were loaded on gels after completion of 20 cycles. Because the target flanked by WYR2 and WYR4 is highly repeated in male, but not in female DNA, these results suggest that the target is located on the Y chromosome. However, after 40 or 45 amplification cycles, a band in the target size interval became apparent in samples containing only female cells.

The results of these studies of WYR2 and WYR4 indicate that the female genome contains a small number of copies of the amplification target. These primers allow sexing of fetal cells in samples such as cord blood, chorionic villus samples or amniocyte cultures by performing a limited number of amplification cycles, such as the above mentioned 20 cycles. Aliquots of the PCR samples are taken after 20 cycles and subjected to gel electrophoresis or other detection schemes. Samples containing male cells show the band in the target size region, whereas samples with only female DNA do not show a band. The amplification of target DNA in this samples can be continued to verify negative results from the 20 cycles amplifications. The appearance of the bands in the target size region after approximately 40 cycles in all samples can be used as a control of PCR conditions and can be applied to exclude false negative results from 20 cycles amplifications. The Gitschier primers behave similarly, that is they have low or limited specificity.

The polymerase chain reaction process can be accomplished in a discontinuous step-wise fashion as has been demonstrated by a number of researchers in the field. Examples of this approach to PCR is shown in the Mullis patents (U.S. Pat. No. 4,683,195 issued Jul. 28, 1987, and U.S. Pat. No. 4,683,202 issued Jul. 28, 1987), which are hereby incorporated by reference. There are a number of well-known DNA polymerases which can be successfully employed in various PCR methods, such as those listed in the 1989 Sigma catalog (1989 Sigma Cytochemical Catalog, pp. 1028–1029). Other PCR methods and reagents may also be employed.

A PCR method better suited to large scale assay processing is an automated programmable system. One such system has been developed by the inventors (*DNA*, Vol. 7, No. 6, pp. 441–447, 1988). This article also describes the use of a thermostable DNA polymerase which is particularly suited to the production of the subject DNA probe and to the amplification of the test sample material. A graph displaying temperature changes during the process used in the present examples is set forth in FIG. 5.

Prior to amplification, restriction enzymes are often employed to cut the nucleic acid into smaller pieces and to digest non-target sequences. The restriction enzymes used must be chosen to assure that they will not cause breaks within the target or primer sequences but will none the less effectively digest undesirable sequences. The preferred restriction enzymes for some uses are set out in the example section below. Virtually any restrictive enzyme can be used depending on the particular requirement involved. These can include those listed in the Sigma catalog, among others (1989 Sigma Biochemical catalog, pp. 1008–1027).

PCR primers produced by the method of the present invention have a number of uses outside gender assay probe development. When paired with a sister primer some substantial length downstream, a very long nucleic acid strand is produced. While such strands are likely not suitable for gender determination, they have numerous other uses. By way of example, when appropriately labeled these sequences can serve as Y chromosome painting or decorating material. This provides a tagging method by which to observe translocations and deletions in the distal arm regions of the Y chromosome.

Other Methods

There are a number of alternatives to the PCR method for identifying and producing the probes of the subject invention. As can be seen from the above discussion, the selection of the appropriate probe sequences is a matter of reviewing large maps of the repetitive sequences in the Y chromosome, and selecting the most promising probe sequences from within those maps. This selection process requires balancing the factors as discussed above with the needs of a particular anticipated use of the probe.

When the probe sequence has been selected, it may be produced by any number of procedures well-known in the art. For instance, one could simply synthesize it using well-known procedures or automatic synthesizing machines, such as that described by M. H. Caruthers. "Gene Synthesis Machines: DNA Chemistry and its Uses." (*Science*, Vol. 230, pp. 281–285, 1985).

There are several other methods beyond PCR technology which can be used to specifically amplify DNA sequences. These include, among others, "Isothermal Techniques," (Guatell et al., *Proceeding of the National Academy of Science*, Vol. 87, pp. 1874–1878, 1990), "Transcription Based Methods," (Kwoh et al., *Proceeding National Academy of Science*, Vol. 86, pp. 1173–1177, 1989), and "QB Replicase Techniques," (Munishkin et al., *Nature*, Vol. 33, p. 473, 1988).

Once produced, the probe can be used as a template to produce large numbers of copies, again by any of several well-known methods. The corresponding RNA probe can also be produced from this pool of DNA material. Promoter sequences or other useful additions can be attached to the RNA and DNA probes of the present invention. Examples of such additions are well-known in the art, and can be coordinated with PCR product production (Kemp et al., *Proceedings of the National Academy of Sciences*, Vol. 86, pp. 2423–2427, 1989). The resulting sequences can be cloned using any one of a number of appropriate vectors or otherwise reproduced to provide multiple copies for use as probes.

Probes produced by any method can be used in a number of ways. The probes can be labeled fluorescently, enzymatically, radioactively, etc. An automated detection system can be set up using column technology or other methods.

EXAMPLE 1

Metaphase Spread Experiments

Probe Production. A 124 base pair DNA segment of the Y chromosome specific 3.4 kb repeat was manufactured using the selection method delineated above. The selected segment encompasses the area of the map in FIG. 1 from bp #3089 to bp #3212.

Primer Construction. Oligonucleotide primers flanking 70 base pair long segments near the 3' end of the Y chromosome specific DNA repeat were synthesized using phosphoramidite chemistry on a DNA-synthesizer. These primers were chosen to be within the identified probe sequences. The primers employed were WYR 2, 4, 5, 6, 7, and 8 as listed in FIG. 3. Synthesis and further purification of the oligonucleotides by reverse phase chromatography and high performance liquid chromatography (HPLC) were performed.

The addition of two 27 bp primers to the 70 bp probe sequence resulted in a 124 bp products. This was the case when WYR2,4, WYR5,6 or WYR 7,8 were employed. When WYR 4 and WYR 6 were combined, a 248 bp product was achieved (see FIG. 2).

DNA Amplification. Approximately 1 $\mu$l of capillary blood from a male donor was washed twice in 500 $\mu$l of distilled water and mixed with the reaction buffer containing the DNA polymerase in preparation of in vitro DNA amplification. The reaction buffer consisted of 5 units of Thermus aquaticus DNA polymerase (Taq polymerase, Perkin Elmer Cetus, Emeryville, Calif., 5 units/$\mu$l, Chien et al., *Journal of Bacteriology*, Vol. 127, p. 1550, 1976) mixed with 100 microliters amplification buffer. This buffer was made of the following: 10 mM Tris-HCl, pH 8.4 at 20° C., 1.5 mM $MgCl_2$, 50 mM KCl, 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 0.2 mM each (all dNTP's were obtained from Pharmacia, Piscataway, N.J.), 1.2 mM each primer.

Mineral oil (100 microliters, SQUIBB) was layered on top of the reaction mix to prevent evaporation during PCR. DNA amplification was performed on an automated thermal cycling system (Weier et al., *DNA*, Vol. 7, p. 441, 1988). Each cycle began with a thermal denaturation step of 120 seconds (180 seconds for the initial denaturation), during which the sample temperature was increased to 94° C. Primer annealing during the second step of each cycle was performed at 46° C. for 150 seconds. The temperature was then increased slowly (0.07° C./seconds) to 72° C. The cycle was completed by holding this temperature for 120 seconds for primer extension. Thus, the total time for each cycle was 9.5 minutes (10.5 for the first cycle). A graphic representation of the cycle is provided in FIG. 5.

Twenty cycles requiring approximately 3 hours were used for initial DNA amplification. DNA fragments in a 10 $\mu$l aliquot of the PCR solution were separated using gel electrophoresis, stained with ethidium bromide and analyzed visually. Amplification of the Y chromosome specific, 124 bp sequence was confirmed by appearance of a single-band in the predicted size interval.

Probe Biotinylation. Unbound dNTP molecules were removed from the PCR solution from the previous 20 cycle amplification by spinning the sample through a 1 ml Sephadex G-50 column (Pharmacia, Pleasant Hill, Calif.) equilibrated with 10 mM Tris-HCl, pH 8.4 at 20° C., 1.5 mM $MgCl_2$, 50 mM KCl. Five $\mu$l aliquots of the PCR solution were resuspended in 275 $\mu$l of biotinylation buffer. This buffer consisted of 10 mM Tris HCl, pH 8.4 at 20° C., 1.5 $MgCl_2$, 50 mM KCl, dATP, dCTP and dGTP, 0.2 mM each, 1.2 mM each primer and 20 units of Taq polymerase.

Five samples were made by addition of different amounts of dTTP (2 mM, 8140A6, Bethesda Research Labs, Gaithersburg, Md.) and Biotin-11-dUTP (5 mM in $H_2O$, SIGMA, St. Louis, Mo.) to the biotinylation buffer. They were devised as listed below.

Sample 1 (100% biotin) 20 $\mu$l Biotin-11-dUTP
Sample 2 (90% biotin) 5 $\mu$l dTTP, 18 $\mu$l Biotin-11-dUTP
Sample 3 (70% biotin) 15 $\mu$l dTTP, 14 $\mu$l Biotin-11-dUTP
Sample 4 (50% biotin) 25 $\mu$l dTTP, 10 $\mu$l Biotin-11-dUTP
Sample 5 (0% biotin) 30 $\mu$l dTTP.

Each tube was capped with 100 $\mu$l of mineral oil and amplified for an additional 20 cycles to generate biotin labeled DNA fragments.

Ten microliter aliquots of the final solutions and two aliquots of 300 mg of DNA sizemarker (O./X174 DNA/Hae III digest, BRL) were loaded on an agarose gel (4% agarose (BRL) in 1×TAE, Maniatis, *Molecular Cloning: a Laboratory Manual*, Cold Spring Harbor, Cold Spring Harbor Laboratory, 1986) after completion of the biotinylation PCR. Gel electrophoresis was performed in 1×TAE containing 0.5 µg/ml ethidium bromide (EB) at 15 V/cm for 50 min.

Melting curves of the double-stranded DNA fragments were recorded on a Gilford 2400 spectrophotometer (Gilford, Oberlin, Ohio) equipped with a Gilford 2527 thermal programmer. Unbound deoxynucleotides were removed from the solutions as described above. The samples were loaded at room temperature into 350 µl quartz glass cuvettes with an optical path length of 1 cm. Readings of the optical density at 260 nm ($OD_{260}$) with a slit width of 0.3 mm were taken while increasing, the temperature at a rate of 1° C./minute until the sample temperature exceeded 90° C.

In Situ Hybridization. Metaphase spreads were made from short-term lymphocyte cultures grown for 72 hours in RPMI 1640 with 20% fetal calf serum, 2% penicillin and 4% phytohemagglutinin (PHA, Gibco, Grand Island, N.Y.) according to the procedure described by Harper et al., (*Proceeding of the National Academy of Science*, Vol. 78, p. 4458,1981). Cell cultures were blocked for 17 hours with methotrexate ($10^{-5}$M, Sigma), followed by incubation in RPMI containing thymidine ($10^{-5}$M, Gibco, Grand Island, N.Y.) for 5 hours. Cells were blocked in mitosis during a 10 minute treatment with colcemid (0.12 µg/ml, Gibco). Cells were harvested and incubated in 75 mM KCl for 15 minutes at 37° C. The cells were spun down and approximately $10^7$ cells were fixed in 5 ml freshly made acetic acid/methanol (1:3). The fixative was changed twice and two drops of the cell suspension were dropped on slides. Slides were air dried and stored under nitrogen in sealed plastic bags in the freezer (−20° C.) until used.

Chromosomes and cells on slides were denatured for 2 minutes at 70° C. in 70% formamide (IBI, New Haven, Conn.), 2×SSC (0.3 M Na citrate, Sigma), pH 7.0, prior to addition of the hybridization mixture. One microliter of each of the biotin labeled probes and the unlabeled control (sample 5) was added without purification to 19 µl of the hybridization mix described by Pinkel et al., (*Cold Spring Harbor Symposia on Quantitative Biology*, Vol. Li, p. 151, 1986), so that the final concentration was 50% formamide, 10% dextran sulfate, 50 ng/µl herring sperm DNA, 2×ssd, pH 7.0. Each probe mix was denatured at 70° C. for 5 minutes.

The mix was then added to the metaphase spreads, covered by a 22 mm by 40 mm overslip and hybridized overnight at 37° C. The sides were subsequently washed in 50% formamide, 2×SSC, pH 7.0 at 45° C. for 20 minutes each and several changes PN buffer (0.1M sodium phosphate, pH 8.0, 0.1% NP40) at room temperature. Biotin was detected with a 20 minute incubation in Avidin-FITC (Vector Laboratory, Berlingame, Calif.), 5 µg/ml in PN buffer plus 5% nonfat dry milk at room temperature. Excess Avidin-FITC was removed by two changes of PN buffer at room temperature, and the chromosomes and cells were counterstained with propidium iodide (PI, 2 µg/ml, Sigma) in antifade solution (Johnson, *J. Immunol Methods*, Vol. 43, p.349,1981).

Photographs were taken on Kodak Ektachrom 400 film with a Zeiss AXIOPHOT fluorescence microscope (Zeiss, Oberkochen, FRG) equipped with a PlanNeofluar 100×/1.30 Oil objective. This photograph is included in the present application as FIG. 6.

Figure 7:
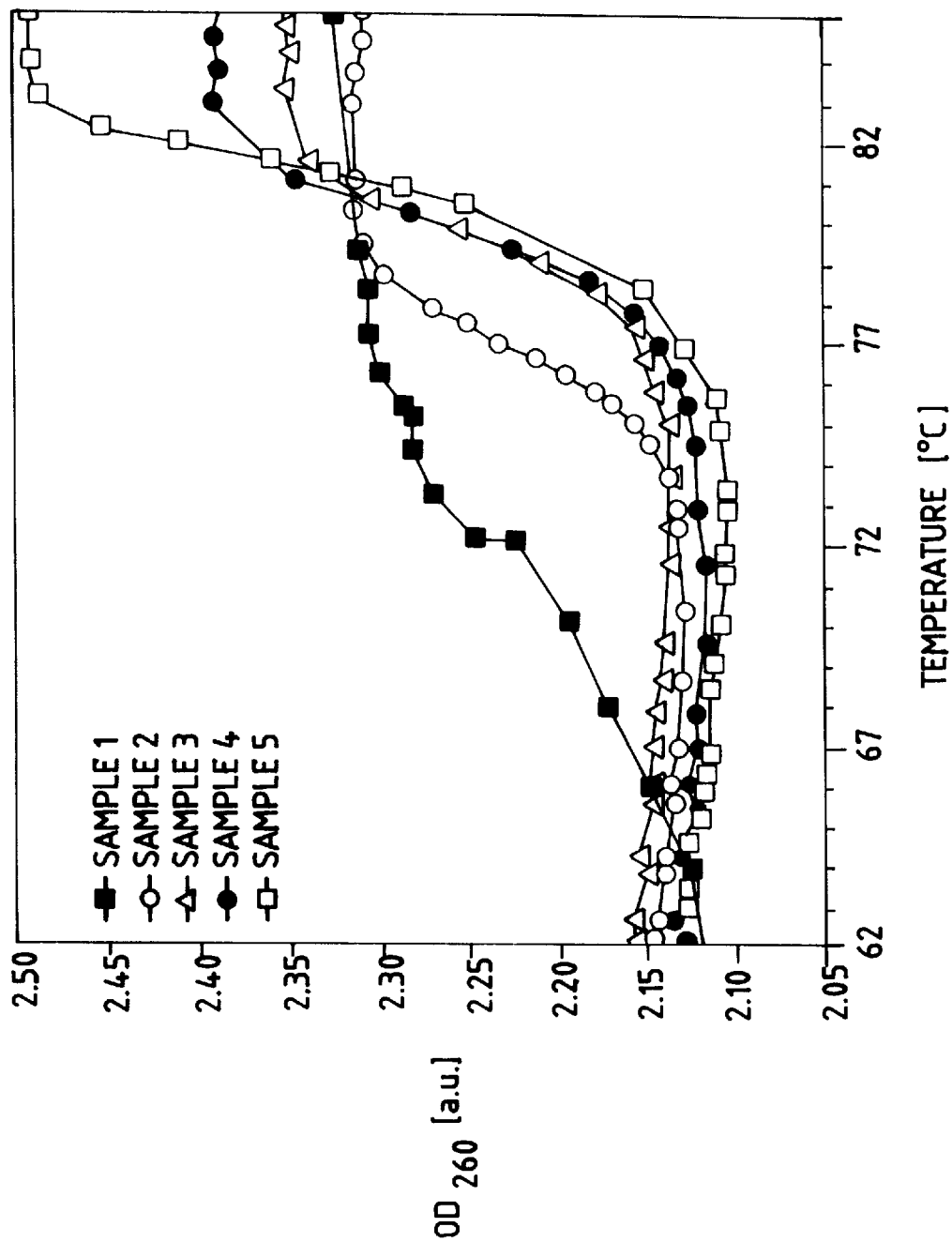
FIG. 7—is a graph of melting temperature of DNA samples biotinylated in the presence of different amounts of biotin-11-dUTP.
Figure 8:
FIG. 8—is a photograph showing the results of gel electrophorese of several DNA samples.

Results. The results of the gel electrophoresis are shown in FIG. 7 and photographs are provided in FIG. 8. Strong bands were observed, indicting the successful amplification of the target DNA sequence. Lane 1 shows the product resulting from the PCR in the presence of dTTP (sample 5, 0% biotin). The band occurred at approximately 124 bp as expected. Lanes 2–5 show PCR products after 20 additional cycles in the presence of various concentration of Biotin-11-dUTP. These DNA fragments migrated more slowly than the 124 bp DNA in Lane 1. This was to be expected since the incorporated biotin slows the rate of migration of the labeled DNA (Foster, *Nucleic Acid Research*, Vol. 13, p. 745, 1985). The electrophoretic mobility decreased with increasing molar ratio of Biotin-11-dUTP to dTTP.

A melting temperature of 80.8° C. was observed for the unlabeled duplex (sample 5, 0% biotin). The melting curve for the fully biotinylated DNA (sample 1, 100% biotin) was much broader than that for the unlabeled sample and shows a melting temperature of approximately 70.5° C. Melting temperatures of doubled-stranded DNA fragments with lower molar ratio of Biotin-11-dlJT/dTIP during biotinylation, were determined to 79.7° C. for sample 4 (50% biotin), 79.2° C. for sample 3 (70% biotin) and 76.2° C. for sample 2 (90% biotin).

Figure 6B:
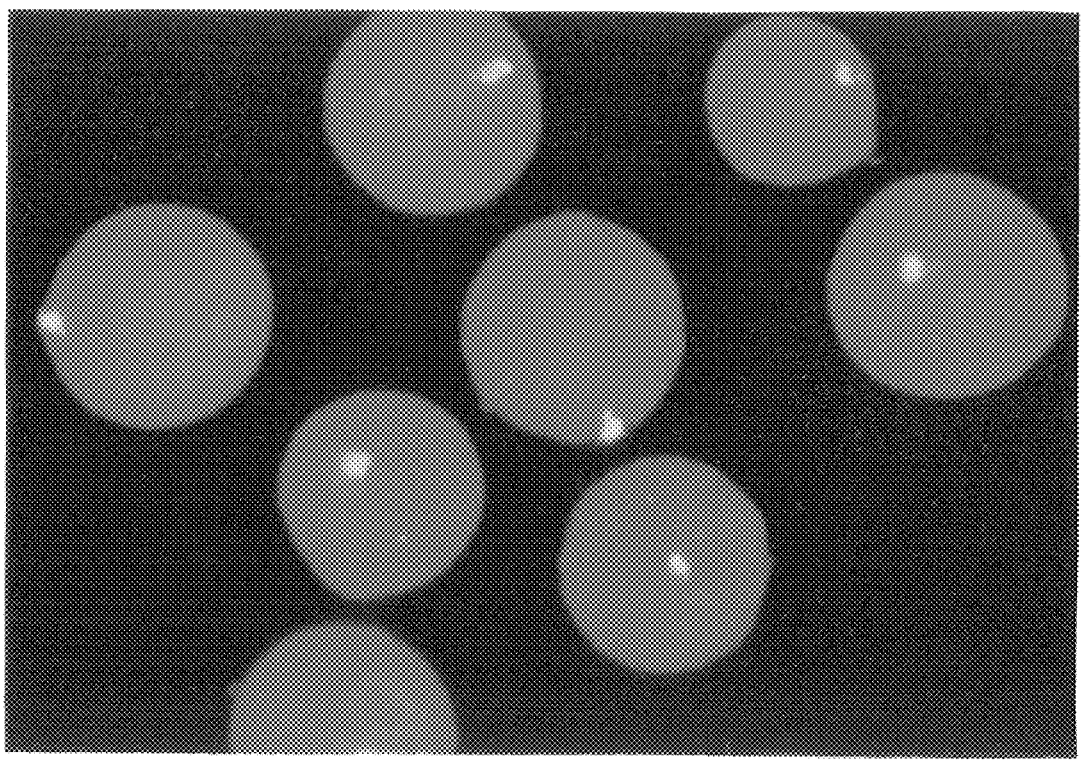
FIG. 6(b)—shows the cells labeled with the inventive probe in the interphase stage of cell division in blood from male volunteers.

The PCR products resulting from the 20 cycle biotinylation reaction were used for in situ hybridization without further purification. FIG. 6 shows the results of hybridization of an aliquot of sample 1 (100% biotin) to a metaphase spread from a male lymphocyte. All chromosomes fluoresce red due to the propidium iodide (PI) staining. Fluorescence from the hybridized probe appears yellow in the photograph (red from the PI plus green from the avidin-FITC). The probe fluorescence is observed on the distal end of the long arm of the Y chromosome as expected (Nakahori, *Nucleic Acid Research*, Vol. 14, p. 7569,1986). No yellow fluorescence was detected on any of the other chromosomes. Interphase nuclei that were present in the preparation hybridized with the Y specific probe also showed an area of strong yellow fluorescence (FIG. 6(*b*)). This cluster of FITC fluorescence was detectable in all hybridized nuclei from the male donor. Hybridization with this probe to cells from a female donor showed no detectable probe binding. Five hundred thousand cells were analyzed, with none showing probe binding.

In situ hybridization of aliquots of sample 2 and 3 showed a slight increase in fluorescence intensity. When probe 4 was hybridized with metaphase chromosomes (FIG. 6(*a*)) the biotin-avidin/FITC labeled hybridization spots appeared less dense on the long arm of the Y chromosomes. An increased amount of unspecific binding of biotinylated probe was observed with samples 2, 3, and 4, although the Y chromosome can be easily identified in metaphase spreads. Interphase nuclei hybridized with probe 2, 3, and 4 show a number of small, secondary areas of probe binding. Hybridization with the control (FIG. 6*e*, sample 5, 0% biotin) revealed no specific binding of avidin/FITC to the genomic DNA.

EXAMPLE 2

Artificial Mixing Studies

Sample Preparation. For the first set of trials to determine the limits of detectability of the probe system, male cells were mixed with female cells to a variety of dilutions.

Peripheral blood samples were taken using heparinized or EDTA treated sample tubes from researchers who served as volunteer blood donors for this work. Beyond both sexes being used as donors, the volunteers were of varied ethnic backgrounds, demonstrating the universal applicability of the successful sex identification which was accomplished as specified below. The blood was stored at room temperature for less than 24 hours prior to preparation for the testing procedure. Most samples were used immediately.

Male and female cells were artificially mixed at varying percentages. They were double-coded to assure impartiality of the researchers doing the testing. The code was not broken until the results of the test were completed.

The mixed, coded blood samples were aliquoted in volumes of less that 5 ml into 15 ml tubes. A 4 ml volume of density gradient medium (Sepracell) was added. The tubes were capped, inverted several times, and centrifuged at 4000 g (2300 rpm) for 30 minutes at 25° C. Three fractions were produced. The top fraction (about 2 ml) contained serum and other blood materials. This layer was decanted. The meniscus over the remaining red blood cell fraction contained the WBCs.

This leucocyte fraction was then transferred to new tubes and mixed with 15 ml cold PBA (PBS+0.1% BSA, pH 7.2). Following resuspension, the tubes were spun at 1200 rpm for 15 minutes at 25° C. The resulting pellet was aspirated and resuspended in 10 ml cold PBA. The tube was then spun at 300 g for 15 minutes at 10° C.

The material in the tube was then aspirated and the pellet resuspended in 5 ml 0.25% paraformaldehyde/PBS (phosphate buffered saline) at pH 7.2. The paraformaldehyde treatment was to prepare the materials for cytological analysis, and may generally be omitted when PCR analysis alone will be practiced.

The material was left to rest at 25° C. for 15 minutes, and then spun at 300 g (800 rpm) for 10 minutes at 10° C. The resulting pellet was aspirated and resuspended in PBS, spun at 300 g (800 rpm) for 10 minutes at 10° C. The supernatant was then discarded.

The resulting WBC concentration was determined with a hemocytometer. Aliquots of $10^6$ cells were deposited in 0.5 ml microcentrifuge (Eppendorf) tubes.

Two hundred fifty $\mu$l of freshly prepared Carnoy's fixative (1 part glacial acetic acid to 3 parts methanol) were then added to each sample. The material was left at room temperature for 10 minutes. The fixative mixture was freshly prepared to maintain its acetic acid component at the most advantageous level. This fixation step was used to remove a number of proteinaceous components of the blood. It also left the DNA of the WBCs in a more exposed position which is an advantage in the probe step.

The material was then centrifuged at 2000 g for 10 minutes at room temperature, the supernatant discarded, and the pellet resuspended in 500 $\mu$l distilled water. The tube was then spun at 12000 g for 15 minutes at room temperature, and the supernatant discarded. The pellet was again resuspended in 500 $\mu$l $H_2O$, centrifuged at 1200 g for 15 minutes at room temperature and the supernatant discarded. This repeated step served to remove the lysed materials and the fixatives, which might otherwise have interfered with the PCR assay.

The resulting sample were dried in a Speedvac concentrator. The samples were then stored at −18° C. until they were needed for use. These materials can be stored for a year or longer prior to advancing to the next step in the procedure.

PCR Procedure. 50 $\mu$l of a reaction mixture was added to the sample. The reaction mixture was made of 10 mM Tris-HCl, pH 8.4, 50 mM KCl, 1.5 mM $MgCl_2$, 0.2 mM each dATP, dCTP, dGTP, and dTTP, containing 1 unit Thermus aquaticus DNA polymerase (Taq, Perkin Elmer Cetus, Norwalk) and 60 pmoles each primer WYR4, WYR6 were added to the samples.

The restriction enzymes and DNA polymerase were then added as follows: 5 units Sau 3A (BRL), 5 units Hae III (BRL). The materials were mixed spun down briefly and a layer of 50 $\mu$l mineral oil was placed on the top of the sample. The sample tube was then closed for the remainder of the operation.

Contamination by the cells of male technicians or other source of male DNA was a potentially complicating factor in this assay. Therefore, to minimize handling, the restriction enzyme and polymerase steps were done without any additional entry into the test vial. This was accomplished by adding both the restriction enzyme material and primer reagents prior to incubation and changing the activating temperature in order to induce the stage of the process desired. The automated aspect of this process is shown schematically in FIG. 5.

For the first reaction, the vials were maintained at 37° C. for a period of 60 minutes. At that point, thorough digestion of the DNA strands at the appropriate sites had occurred, but the thermostable DNA polymerase was not active because of the low temperature. For the second reaction, the temperature of the vial was raised from 37° C. to 94° C. On the other hand, the thermostable polymerase was then active, and the amplification reaction was initiated and sustained. By combining the reactions, the products of the original cleavage process actually serve as a source of materials in the polymerization process.

Following the initial 60 minute digestion period, the samples were placed in an automated thermal cycler and 45 PCR cycles were performed. Each cycle began with a thermal denaturation step of 120 seconds (180 seconds for the initial denaturation) during which the sample temperature was increased and held at 94° C.

Primer annealing during the second step of each cycle was performed at 55° C. for 60 seconds. It was during this low temperature step that the primer DNA annealing is accomplished and the complex became stable. The temperature was then increased slowly (within 2 minutes, 0.14° C./seconds) to 72° C. As such, this was a critical step in the procedure. The cycle was completed by holding this temperature for 120 seconds allowing primer extension.

Using the inventive procedure described above, the inventors achieved a 70–80% extension efficiency rate.

After the last cycle, the sample temperature was held at 72° C. for 5 minutes before the samples were allowed to cool down to 25° C.

Assay. Aliquots of the reagent, usually 5–10 $\mu$l, were loaded on 4% agarose gel and were subjected to electrophoresis for 40–60 minutes at 10 V/cm in 1×TAE (Tris acetate/EDTA buffer (ibid Maniatis et al.) 0.5 $\mu$g/ml ethidium bromide. The target amplification was verified by the appearance of a DNA band in the expected size region (248 bp).

| | First Trial | |
|---|---|---|
| | Ratio Male to Female Cells | Results |
| Sample 1 | 1:1 | Target Amplification |
| Sample 2 | 1:$10^3$ | Target Amplification |
| Sample 3 | 1:$10^4$ | Target Amplification |
| Sample 4 | 1:$10^5$ | Target Amplification |
| Sample 5 | 1:$10^6$ | Target Amplification |
| Sample 6 | 0:0 | No Target Amplification |

| | Second Trial | |
|---|---|---|
| | Ratio Male to Female Cells | Results |
| Sample 1 | 1:100 | Target Amplification |
| Sample 2 | 1:10$^3$ | Target Amplification |
| Sample 3 | 1:10$^4$ | Target Amplification |
| Sample 4 | 1:10$^5$ | Target Amplification |
| Sample 5 | 1:10$^6$ | No Target Amplification |
| Sample 6 | 0:0 | No Target Amplification |

EXAMPLE 3

Biological Cloning

In this case one or more restrictions sites are placed on the probe sequence. This allows cloning of the probe of interest in a large copy number without production of downstream sequences that may display nonspecific binding or otherwise compromise the efficiency of the binding of the probe.

The probe is then labeled using florescent dye. If the probe binds to WBCs prepared by Step 1 in Example 2, then there is positive identification of the fetus as male.

EXAMPLE 4

RNA Probes

In this case one or more RNA polymerase promotor sequences are placed on the probe sequence. This allows transcription of the probe of interest in either or both directions in order to generate single-stranded RNA probe molecules. Probe labeling can be performed by incorporation of labeled nucleotide triphosphates during in vitro transcription by RNA polymerase.

What is claimed is:

1. A method of producing a nucleic acid probe capable of identifying a human Y chromosome, comprising:
   a. synthesizing a nucleic acid strand homologous to at least one highly repeated regions of the human Y chromosome to produce one or more nucleic acids each having a base pair sequence homologous to at least one highly repeated region of the human Y chromosome,
   b. replicating said one or more nucleic acids by a polymerase chain reaction (PCR) processing, provided that twenty (20) or less cycles of PCR amplification are used, and
   c. adding reporter molecules to said one or more nucleic acids.

2. The method of claim 1, wherein the probes are produced by PCR by use of the following primers individually or in pairs:
   WYR 2 ATTCCGTACGATTCCATTCCTTTTGAA
   WYR 4 GAATGTATTAGAATGTAATGAACTTTA
   WYR 5 GGATTCTAATGGAATGGAATTAAATGG
   WYR 6 TTCCATTCCATTCCATTCCTTCCTTT
   WYR 7 TGGGCTGGAATGGAAAGGAATCGAAAC
   WYR 8 TCCATTCGATTCCATTTTTTTCGAGAA
   WYR 9 ATGGAATTGAATGGAACGGAATAGAGT
   WYR 10 CGATTCCATTCAATTCGAGACCATTCT.

3. The method of claim 2, wherein the primers are paired as indicated in FIG. 4.

4. The method of claim 2, wherein said PCR processing includes, (the barely necessary steps),
   a. adding a reaction mixture containing DNA polymerase to the sample,
   b. adding primer to the mixture of step a,
   c. thermocycling the mixture.

Figure 5:
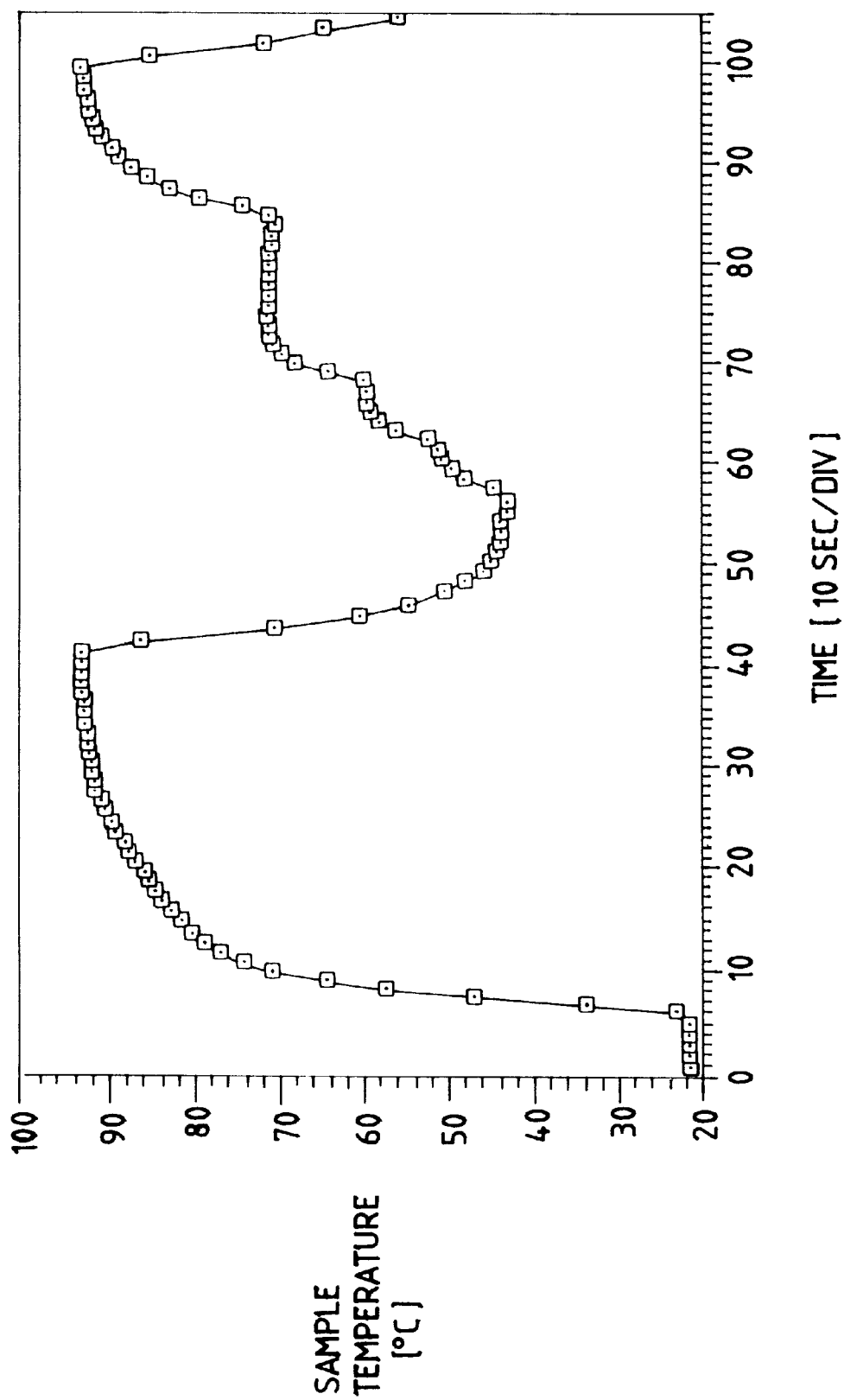
FIG. 5—is a diagram indicating the preferred PCR processing regimen for the inventive probes.

5. The method of claim 4, wherein the steps are carried our as indicated in FIG. 5.

6. The method of claim 4, wherein some or all of the steps are accomplished by automated means.

7. A method of identifying the presence of Y chromosome nucleic acid sequences comprising,
   a. combining the test sample with the DNA probe of claim 1,
   b. testing for the binding of the probe to the test sample material.

8. The method of claim 7, wherein the binding of the probe to the test sample is observed by one of the group of formation of a sediment, competitive inhibition of binding to a haphen to the probe, floroscopic or photometric means, or testing for an indicator molecule which has been attached to or incorporated into the probe.

9. The method of claim 8, wherein the indicator molecule is biotin, flurochrome, Gold, Au, alkaline phosphotase, and/or horseradish peroxidase.

10. The method of claim 7, wherein the sample is maternal blood enriched for fetal cells, sperm, fetal tissue from amniocentesis, cord blood, or chorionic villi sampling, forensic samples, palentology samples, other human tissues, or animal husbandry samples.

11. The method of claim 7, wherein the sample is cells from a transplant patient, cells from a patient being tested for the presence or level of the presence of cancer, male cells intransquire animals, or are in vivo or in vetro biological dosimetry samples.

12. A test kit for the identification of Y chromosome nucleic acid sequences comprising in at least one container the nucleic acid probe of claim 1.

* * * * *